(12) United States Patent
Liaw et al.

(10) Patent No.: US 8,981,038 B2
(45) Date of Patent: Mar. 17, 2015

(54) DINITRO MONOMER, DIAMINE MONOMER, POLYIMIDE AND MODIFIED POLYIMIDE

(71) Applicant: Taiwan Textile Research Institute, New Taipei (TW)

(72) Inventors: Der-Jang Liaw, Taichung (TW); Wen-Hsiang Chen, New Taipei (TW); Ying-Chi Huang, Taipei (TW); Bo-Cheng Tao, Kaohsiung (TW)

(73) Assignee: Taiwan Textile Research Institute, New Taipei (TW)

( * ) Notice: Subject to any disclaimer, the term of this patent is extended or adjusted under 35 U.S.C. 154(b) by 154 days.

(21) Appl. No.: 13/726,552

(22) Filed: Dec. 25, 2012

(65) Prior Publication Data

US 2014/0179878 A1    Jun. 26, 2014

(51) Int. Cl.
*C08G 73/10* (2006.01)
*C07D 213/26* (2006.01)
*C07D 213/38* (2006.01)

(52) U.S. Cl.
CPC .......... *C08G 73/1007* (2013.01); *C07D 213/26* (2013.01); *C07D 213/38* (2013.01); *C08G 73/1085* (2013.01)
USPC ............... 528/310; 528/73; 528/96; 528/170; 528/354

(58) Field of Classification Search
CPC ............................ C08G 73/10; C08G 73/1085
USPC ............... 528/73, 96, 170, 310, 354; 564/305
See application file for complete search history.

(56) References Cited

PUBLICATIONS

Tamami et al., "Preparation and Properties of Novel Polyimides Derived from 4-Aryl-2,6 Bis(4-amino phenyl) pyridine," Journal of Polymer Science: Part A: Polymer Chemistry 39(21), Nov. 1, 2001, pp. 3826-3831.
Zhang et al., "Study on synthesis and characterization of novel polyimides derived from 2,6-Bis(3-aminobenzoyl) pyridine," European Polymer Journal 41(5), May 2005, pp. 1097-1107.
Liu et al., "New Liquid-Crystal Alignment Agents Based on Fluorinated Polyimides with Trifluoromethyl-Substituted Benzene or Diphenylether in the Side Chain," Journal of Polymer Science: Part A: Polymer Chemistry 40(10), May 15, 2002, pp. 1583-1593.
Liaw et al., "Synthesis and Characterization of Novel Diamine and Polyimides Containing Pyridine Heterocyclic and Bromic Functional Groups," The 60th Annual Report of CITE, Dec. 15, 2012, pp. 417-424.

*Primary Examiner* — Gregory Listvoyb
(74) *Attorney, Agent, or Firm* — Jianq Chyun IP Office

(57) ABSTRACT

A polyimide including a structure shown as Formula II is provided, wherein X is halogen, $A_1$ is selected from one of Formula 1 to Formula 18, and n is from 2 to 500, -continued
Formula 8
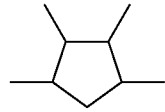
Formula 9
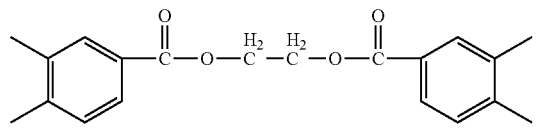
Formula 10
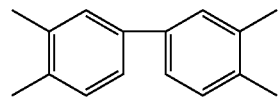
Formula 11
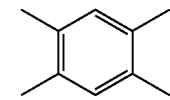
Formula 12
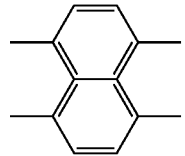
Formula 13
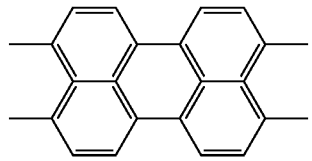
-continued
Formula 14
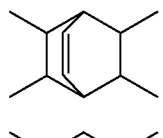
Formula 15
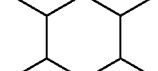
Formula 16
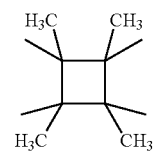
Formula 17
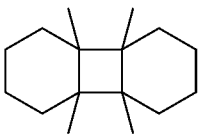
Formula 18
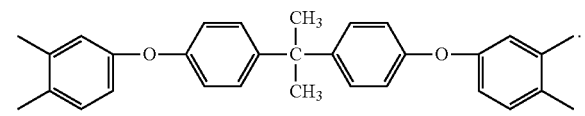
11 Claims, 7 Drawing Sheets

DINITRO MONOMER, DIAMINE MONOMER, POLYIMIDE AND MODIFIED POLYIMIDE

BACKGROUND OF THE INVENTION

1. Field of the Invention

The invention relates to a dinitro monomer, a diamine monomer, a polyimide, and a modified polyimide.

2. Description of Related Art

Generally, polyimide (PI) is a polymer material obtained from the polycondensation reaction between a diamine monomer and a dianhydride monomer. Polyimide contains an imide group, and may be divided into aliphatic and aromatic compounds. In terms of aromatic polyimides, aromatic polyimides have good chemical resistance, mechanical property, and thermal stability, and therefore are widely applied to the semiconductor industry, optoelectronics industry, aeronautical materials, biomedical materials, auto industry, communication materials, mechanical industry, and thin film industry. Furthermore, due to the superior electrical property of polyimide, polyimide is utilized in the semiconductor substrates and in packing materials, and has become an integral material in the cutting-edge technology industry.

So far, polyimide still has some problems in processing and preparation. First, since the melting temperature of polyimide is very high, polyimide may not be processed by hot melting. Moreover, the solubility of polyimide in organic solvents is poor, and even some of the aromatic polyimides may only be dissolved in concentrated sulfuric acid. Since the poor solubility is not conductive to the processability of aromatic polyimides, increasing the processability and applicability of aromatic polyimides by preparing a soluble or thermoplastic polyimide is a current issue that those skilled in the art urgently need to solve.

SUMMARY OF THE INVENTION

The invention provides a dinitro monomer having a heterocyclic pyridine structure.

The invention provides a diamine monomer having a heterocyclic pyridine structure.

The invention provides a polyimide having a reactive group.

The invention provides a modified polyimide having a modified group. As a result, the modified polyimide has good processability and thermal stability.

The invention provides a dinitro monomer including the structure shown in Formula I:

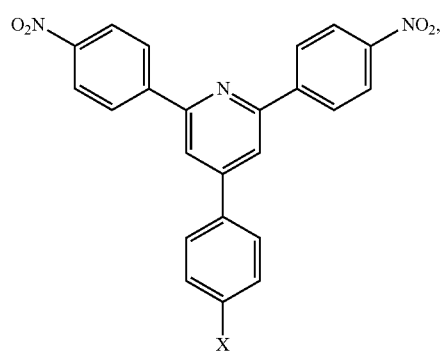

Formula I wherein X is halogen.

The invention provides a diamine monomer including the structure shown in Formula II:

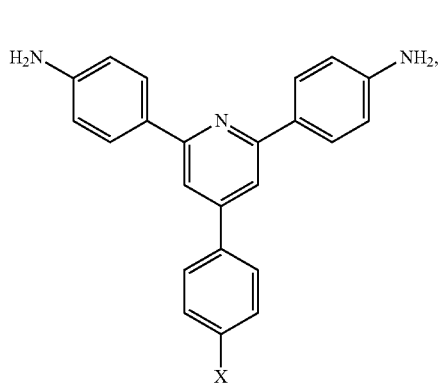

Formula II wherein X is halogen.

The invention provides a polyimide including the structure shown in Formula III:

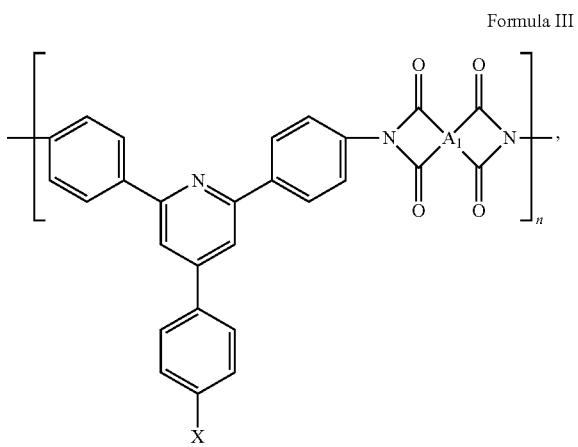

Formula III wherein X is halogen, $A_1$ is selected from one of Formula 1 to Formula 18, and n is 2 to 500,

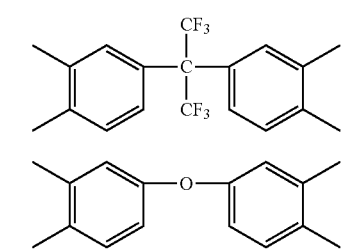

Formula 1

Formula 2

Formula 3
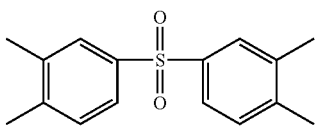
Formula 4
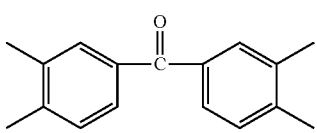
Formula 5
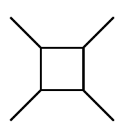
Formula 6
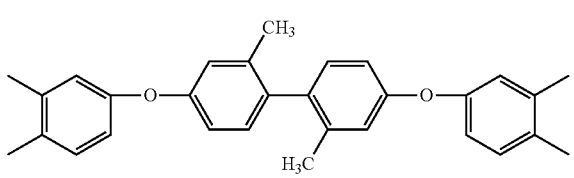
Formula 7
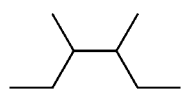
Formula 8
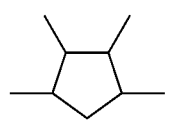
Formula 9
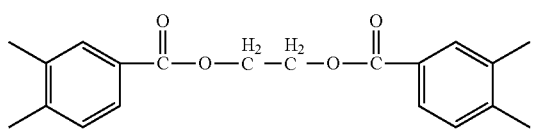
Formula 10
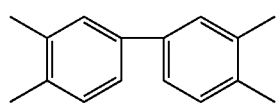
Formula 11
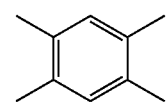
Formula 12
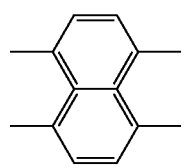
Formula 13
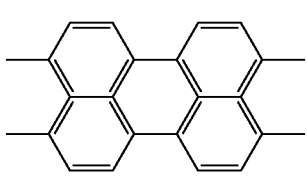
Formula 14
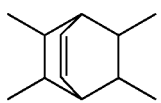
Formula 15
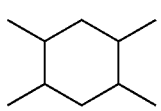
Formula 16
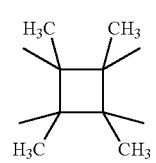
Formula 17
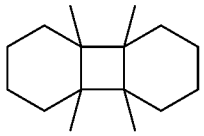
Formula 18
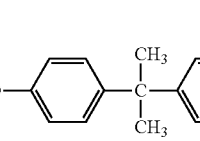
The invention provides a modified polyimide including the structure shown in Formula VI:
Formula VI
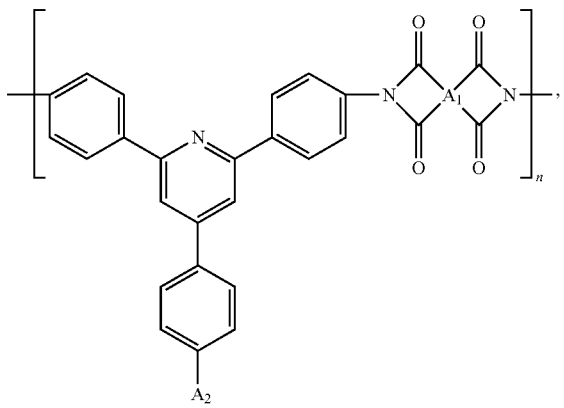
wherein $A_1$ is selected from one of Formula 1 to Formula 18, $A_2$ is selected from one of Formula 19 to Formula 25, and n is 2 to 500,
Formula 1
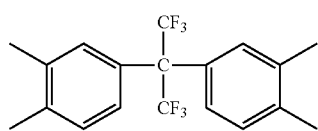

Formula 2
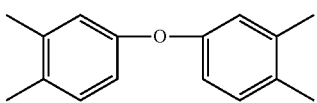
Formula 3
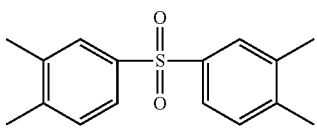
Formula 4
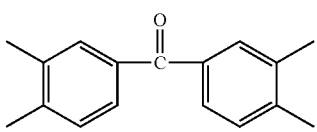
Formula 5
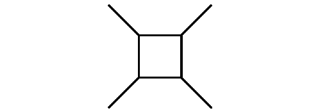
Formula 6
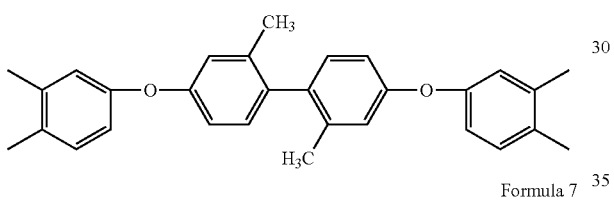
Formula 7
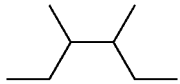
Formula 8
Formula 9
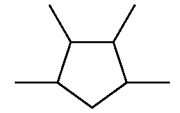
Formula 10
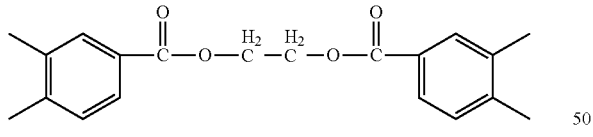
Formula 11
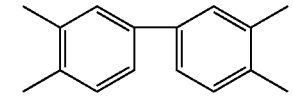
Formula 12
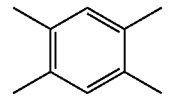
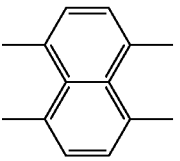
Formula 13
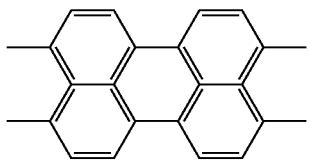
Formula 14
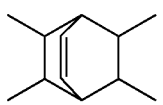
Formula 15
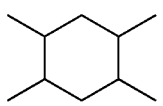
Formula 16
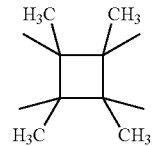
Formula 17
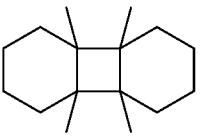
Formula 18
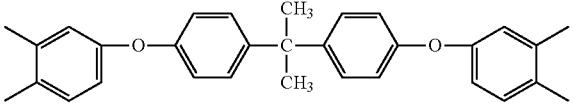
Formula 19
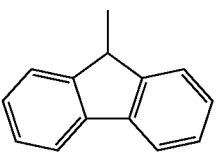
Formula 20
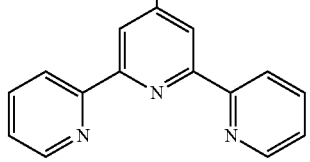

-continued

Formula 21
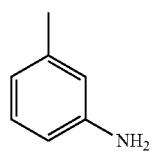

Formula 22
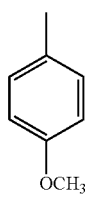

Formula 23
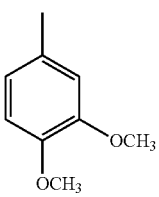

Formula 24
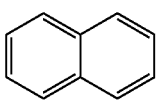

Formula 25
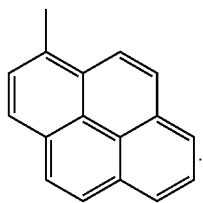

Based on the above, the diamine monomer may be synthesized from the dinitro monomer of the invention, and the polyimide having a reactive group may be synthesized from the diamine monomer, wherein the polyimide having the reactive group may introduce different functional groups to obtain the modified polyimide. The modified polyimide of the invention has good thermal stability and superior processability.

In order to make the aforementioned features and advantages of the invention more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

<Dinitro Monomer>

Figure 1:
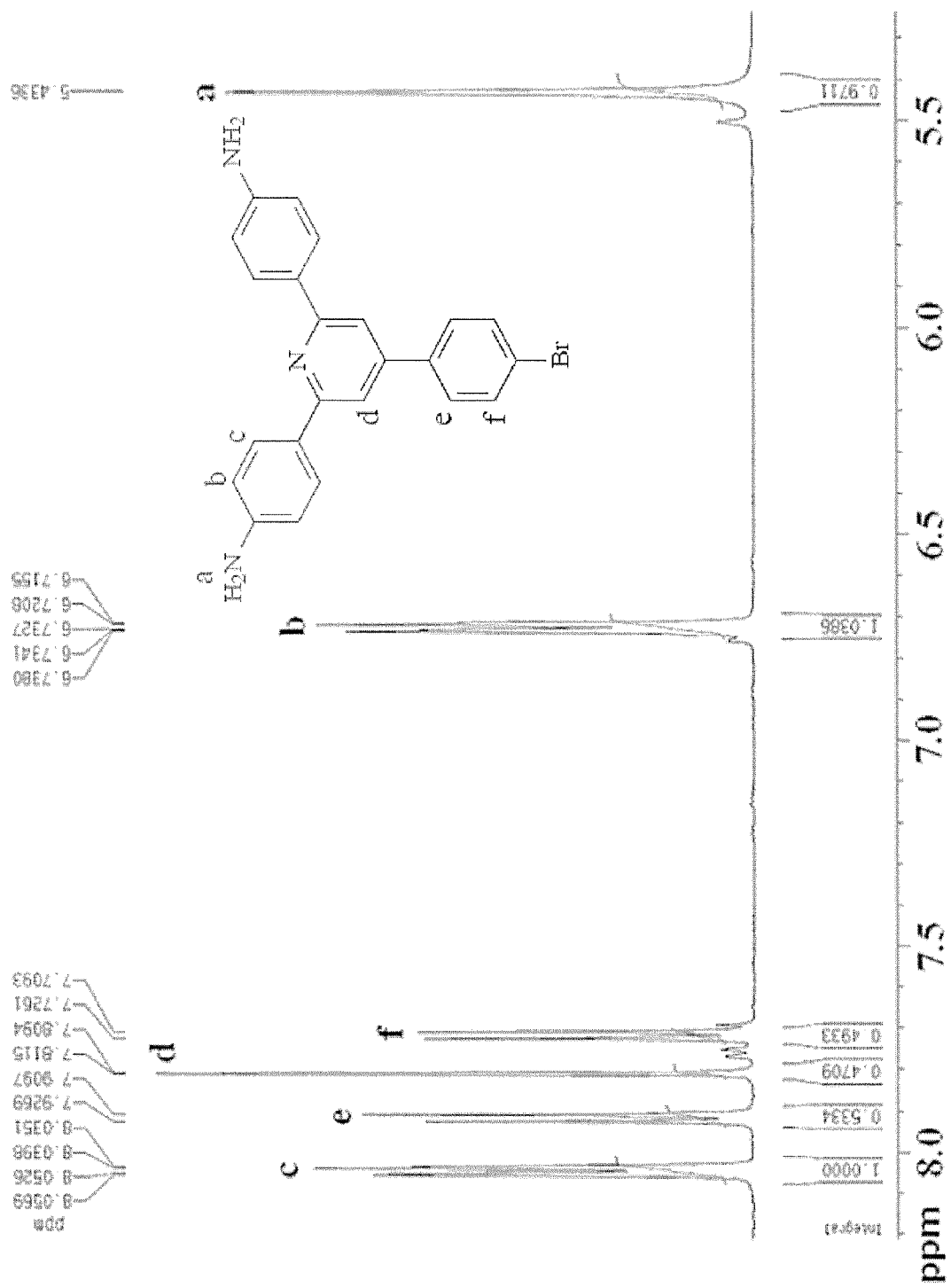
FIG. 1 is a $^1$H-NMR spectrum of diamine compound 2.

The dinitro monomer of the present embodiment includes the structure shown in Formula I:

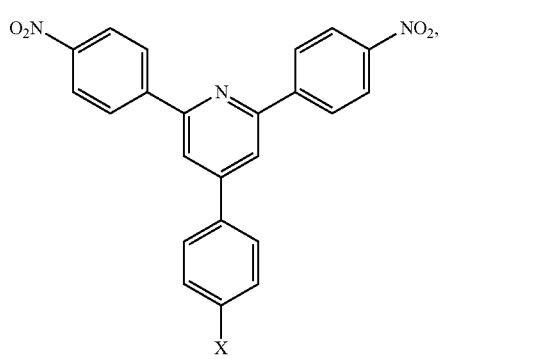

Formula I wherein X is halogen. In other embodiments, X is F, Cl, Br, or I. The dinitro monomer of the present embodiment is a dinitro compound containing a heterocyclic pyridine structure.

<Diamine Monomer>

The diamine monomer of the present embodiment is obtained from the synthesis of the dinitro monomer, and therefore includes the structure shown in Formula II:

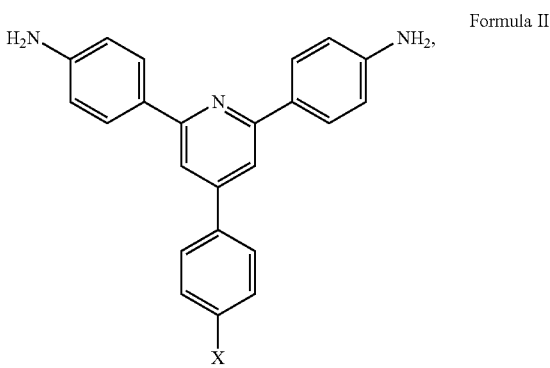

Formula II wherein X is halogen. In other embodiments, X is F, Cl, Br, or I. The diamine monomer of the present embodiment is a diamine compound containing a heterocyclic pyridine structure.

<Polyimide>

The polyimide of the present embodiment is obtained from the synthesis of the diamine monomer, and therefore includes the structure shown in Formula III:

Formula III

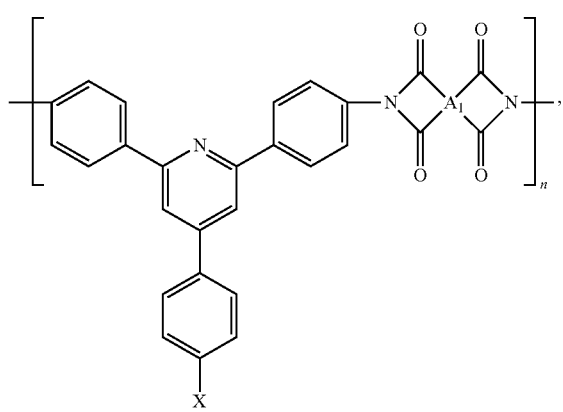

wherein X is halogen, $A_1$ is selected from one of Formula 1 to Formula 18, and n is 2 to 500, Formula 1
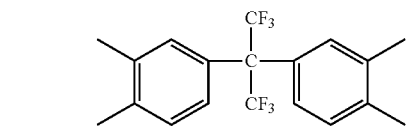

Formula 2
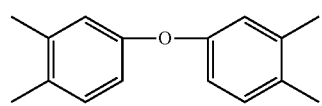

Formula 3
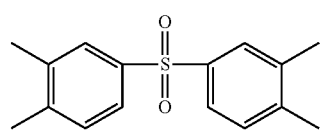

Formula 4
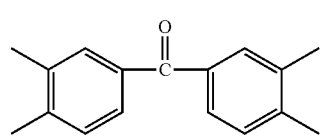

Formula 5
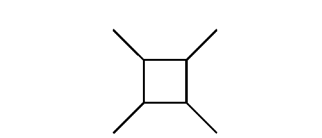

Formula 6
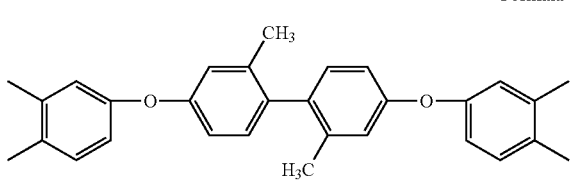

Formula 7
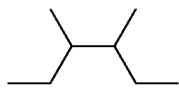

Formula 8
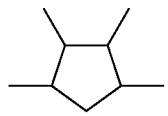

Formula 9
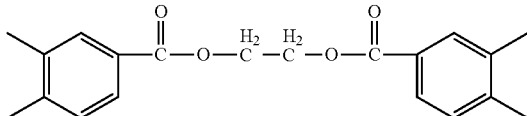

Formula 10
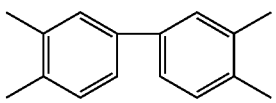

Formula 11
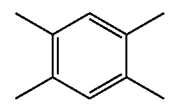

Formula 12
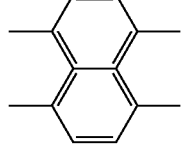

Formula 13
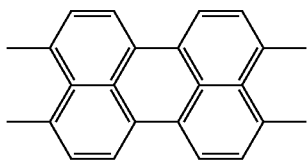

Formula 14
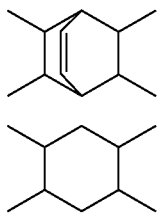

Formula 15
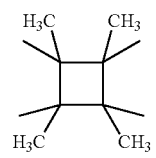

Formula 16
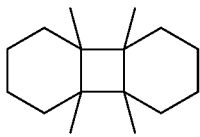

Formula 17
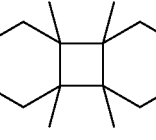

Formula 18

In an embodiment, X is F, Cl, Br, or I. Halogen is a group with good reactivity, and the reactive group may facilitate further reactions of the polyimide, so that the position of the reactive group may be substituted by a functional group.

Accordingly, the characteristics of the polyimide may be modified, such as solubility, thermal stability, oxidation resistance, protonation, alkylation, electron affinity, photochemical and electronic properties, or electron transporting property.

In an embodiment of the invention, the polyimide is as shown in Formula IV:

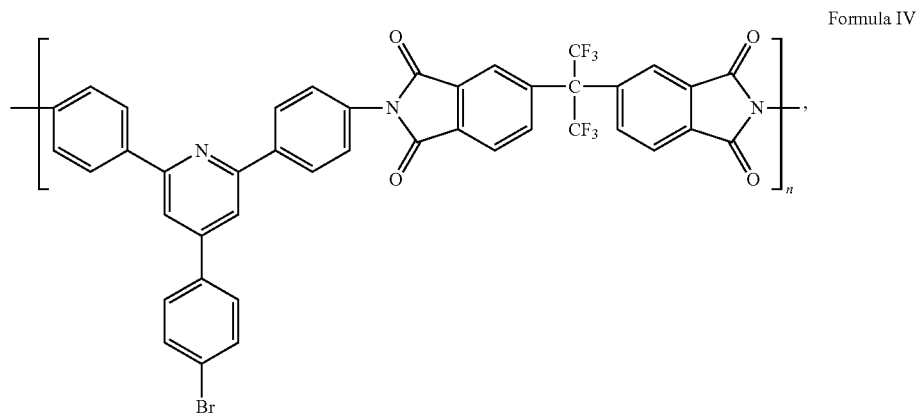

Formula IV wherein n is 2 to 500. The polyimide of the present embodiment has a bromic group and therefore has good solubility in organic solvents. As a result, the polyimide has good processability. Moreover, since the bromic group of the polyimide of the present embodiment has good reactivity, the bromic group may facilitate further reactions and introduce a functional group to adjust the properties of the desired polyimide.

In another embodiment of the invention, the polyimide is as shown in Formula V:

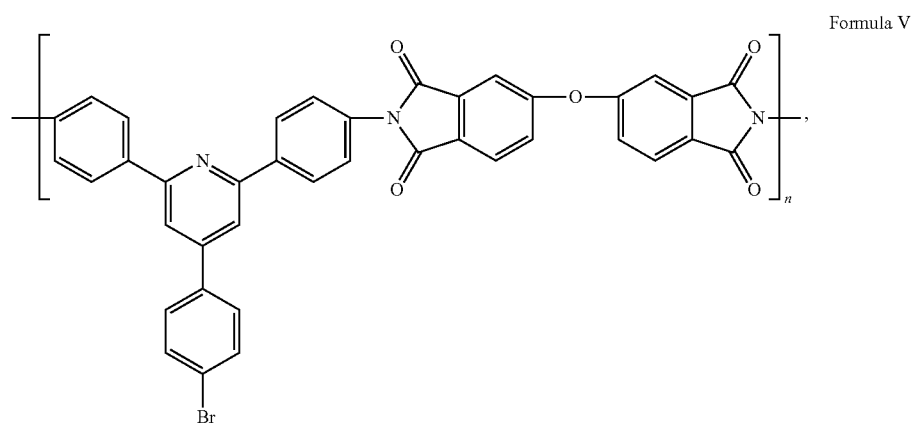

Formula V wherein n is 2 to 500. The polyimide of the present embodiment has a bromic group and therefore has good solubility in organic solvents. As a result, the polyimide has good processability. Moreover, since the bromic group of the polyimide of the present embodiment has good reactivity, the bromic group may facilitate further reactions to introduce a functional group in order to adjust the properties of the desired polyimide.

<Modified Polyimide>

The modified polyimide of the present embodiment is obtained from the modification reaction of the polyimide having a reactive group. Here, a functional group may be introduced into the polyimide frame by the modification reaction to obtain a modified polyimide. The modification reaction is, for instance, Suzuki coupling reaction or another appropriate chemical reaction. When the modification reaction is Suzuki coupling reaction, the X of the polyimide is preferably Br or I.

The modified polyimide of the present embodiment includes the structure shown in Formula VI:

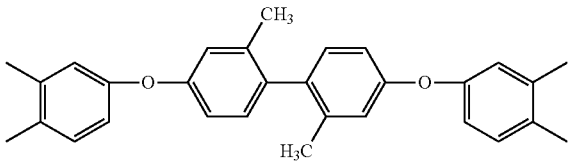

Formula VI wherein $A_1$ is selected from one of Formula 1 to Formula 18, $A_2$ is selected from one of Formula 19 to Formula 25, and n is 2 to 500,

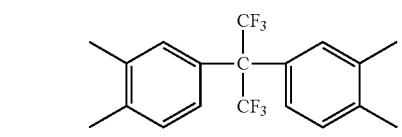

Formula 1

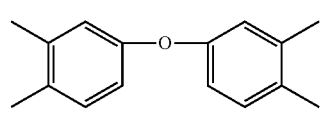

Formula 2

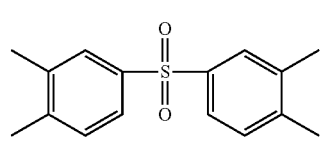

Formula 3

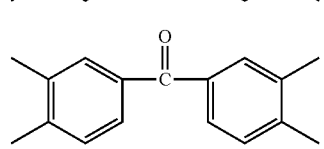

Formula 4

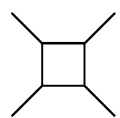

Formula 5

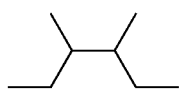

Formula 6

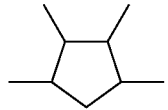

Formula 7

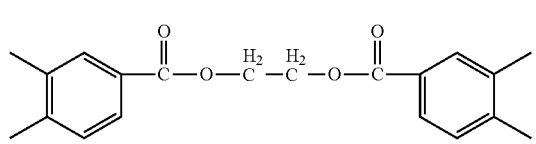

Formula 8

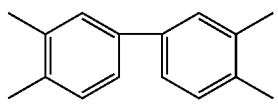

Formula 9

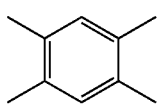

Formula 10

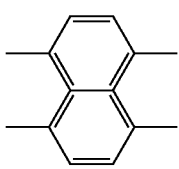

Formula 11

Formula 12

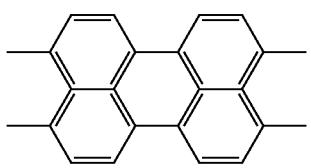

Formula 13

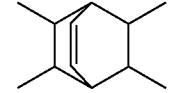

Formula 14

-continued

Formula 15

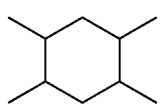

Formula 16

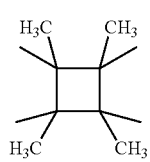

Formula 17

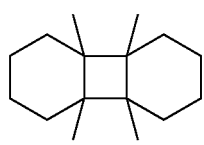

Formula 18

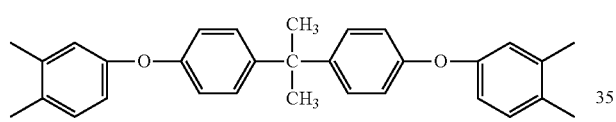

Formula 19

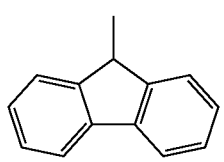

Formula 20

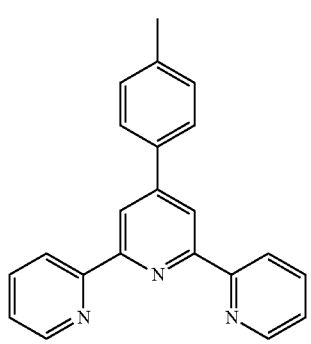

Formula 21

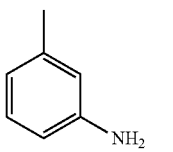

Formula 22

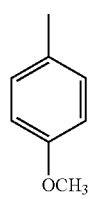

Formula 23

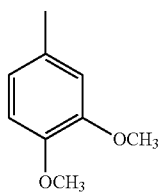

Formula 24

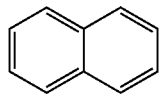

Formula 25

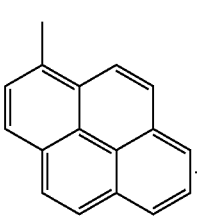

In the present embodiment, the thermal decomposition temperature ($T_d$) of the modified polyimide in nitrogen is 400° C. to 650° C. In an embodiment, the thermal decomposition temperature of the modified polyimide in nitrogen is 530° C. to 545° C. (as shown in Table 6). The thermal decomposition temperature of the modified polyimide in air is 400° C. to 650° C. In an embodiment, the thermal decomposition temperature of the modified polyimide in air is 514° C. to 523° C. (as shown in Table 6). It is acquired that the modified polyimide of the present embodiment has good thermal stability. It should be noted that, the decomposition temperature ($T_d$) of the present embodiment refers to the heating temperature when 10% by weight of the test sample is lost in the thermogravimetry analysis (TGA).

In an embodiment of the invention, the modified polyimide is as shown in Formula VII,

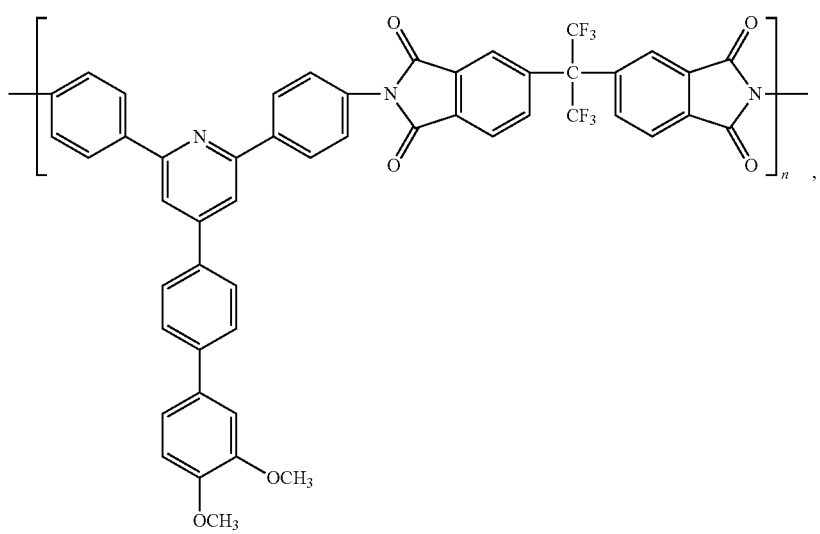

Formula VII wherein n is 2 to 500. The modified polyimide of the present embodiment has good solubility in organic solvents. Moreover, in the present embodiment, an electron donating group is used to substitute the reactive group in polyimide, so that the modified polyimide has stable charge transferability. Therefore, the modified polyimide is suitable as a material for write once read many (WORM) memory devices. Of course, the invention is not limited thereto. In other embodiments, different functional groups may also be used to adjust the characteristics of the modified polyimide.

In another embodiment of the invention, the modified polyimide is as shown in Formula VIII, polyimide is represented. When x is 100%, all of the reactive groups of the polyimide are modified into electron donating groups with each having a methoxy group. Similar to the above embodiment, the modified polyimide of the present embodiment has good solubility and stable charge transferability toward organic solvents, and is suitable as a material for WORM memory devices. Of course, the invention is not limited thereto. In other embodiments, different functional groups may also be used to adjust the characteristics of the modified polyimide.

It should be mentioned that, a certain level of difficulty exists in obtaining the modified polyimide of the present

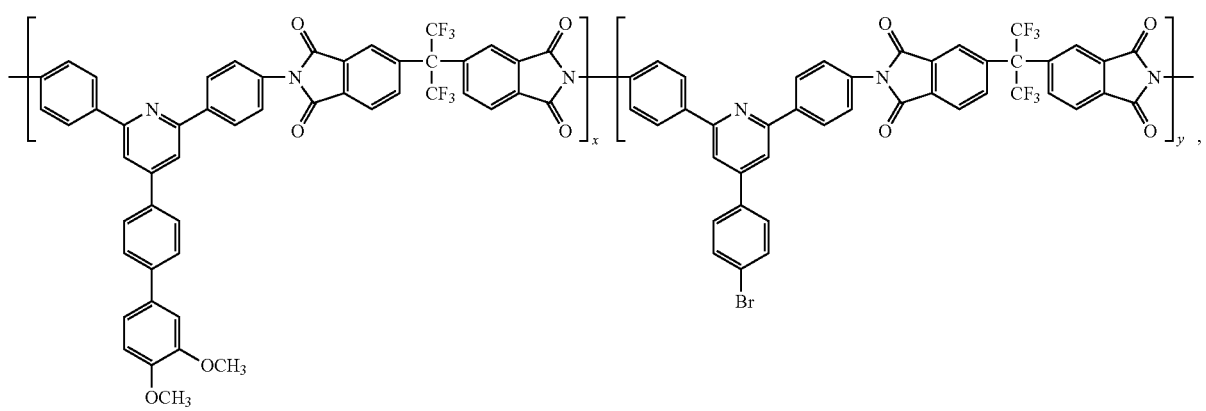

Formula VIII wherein x is 0% to 100%, y is 0% to 100%, and wherein x and y are not both 0%. When y is 100%, unmodified embodiment by synthesizing the monomer molecules. In comparison, in the present embodiment, the polyimide having a reactive group is modified so that a modified polyimide with the desired properties may be more readily obtained.
<Preparation>
Step (1):

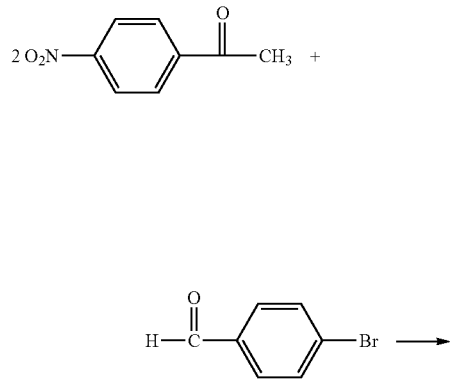

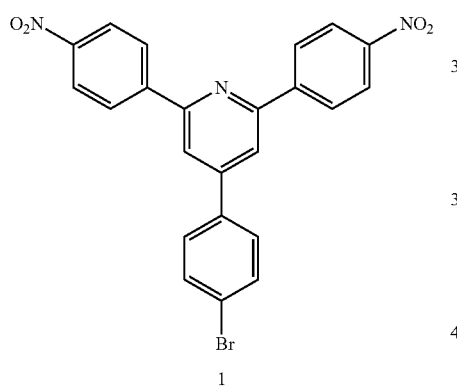

300 ml of glacial acetic acid and 1.2 molar of ammonium acetate are added to 120 mmol of 4'-nitroacetophenone and 60 mmol of 4-bromobenzaldehyde. Then, a reflux is performed at 150° C. for 24 hours, followed by a Chichibabin reaction. After the reaction is complete and the solution is cooled, the solution is filtered to collect the solid. Then, the solid is purified by recrystallization with N,N-dimethyl acetamide to obtain light yellow intermediate product 1. The yield is 45%. The following qualitative tests are performed on intermediate product 1.

Differential scanning calorimetry (DSC): the melting point of intermediate product 1 is greater than 340° C.

Infrared spectroscopy: the characteristic absorption peak of the C=N ring is at 1593 cm$^{-1}$, and the characteristic absorption peak of the N=O is at 1342 cm$^{-1}$.

$^{1}$H-NMR CDCl$_3$: δ(ppm)=8.58-8.57 (4H), 8.40-8.36 (6H), 7.93-7.91 (2H), 7.76-7.74 (2H).

Elemental analysis: theoretical values (%): C=58.00, H=2.96, N=8.82. Analysis Values (%): C=57.76, H=2.95, N=8.74.

Step (2):

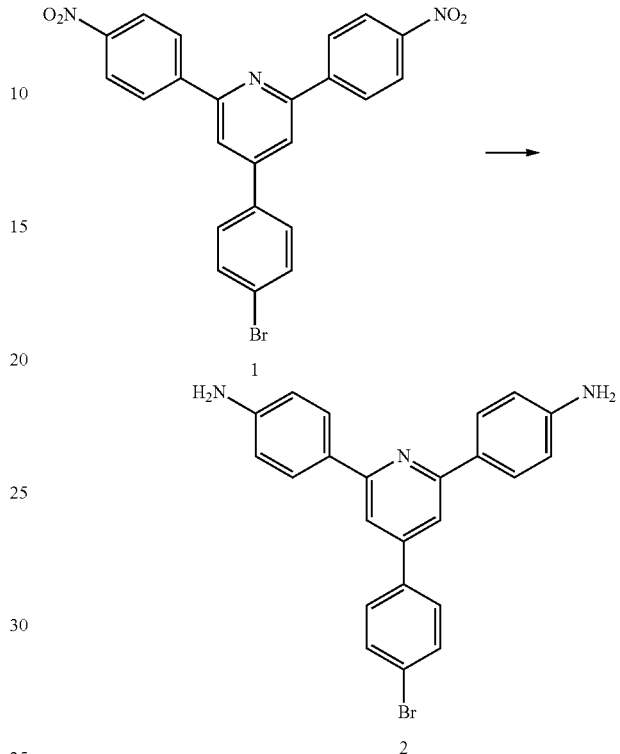

120 ml of ethyl acetate and 50 mmol of SnCl$_2$.2H$_2$O are added to 5 mmol of intermediate product 1. Then, a reduction reaction is performed at 80° C. for 24 hours. After the reaction is complete and the solution is cooled, the pH of the reactive solution is adjusted between 8 and 9 using a 5% aqueous solution of sodium bicarbonate. Then, distilled water is added to the organic phase. After washing a plurality of times, the organic phase solution is isolated. Afterward, the organic phase solution is concentrated to remove the solution in order to obtain the crude product. Then, a plurality of recrystallizations are performed using a tetrahydrofuran/ethanol cosolvent to obtain purified diamine compound 2. The yield is 60%. The following qualitative tests are performed on diamine compound 2.

Differential scanning calorimetry: the melting point of diamine compound 2 is 199° C.

Infrared spectroscopy: the asymmetric stretch characteristic absorption peak of the N—H is at 3438 cm$^{-1}$, the symmetric stretch characteristic absorption peak of the N—H is at 3344 cm$^{-1}$, and the characteristic absorption peak of the C=N ring is at 1593 cm$^{-1}$.

$^{1}$H-NMR DMSO-d$_6$: δ(ppm)=8.05 (4H), 7.92 (2H), 7.81 (2H), 7.72 (2H), 6.73 (4H), 5.43 (4H), as shown in FIG. 1.

Figure 2:
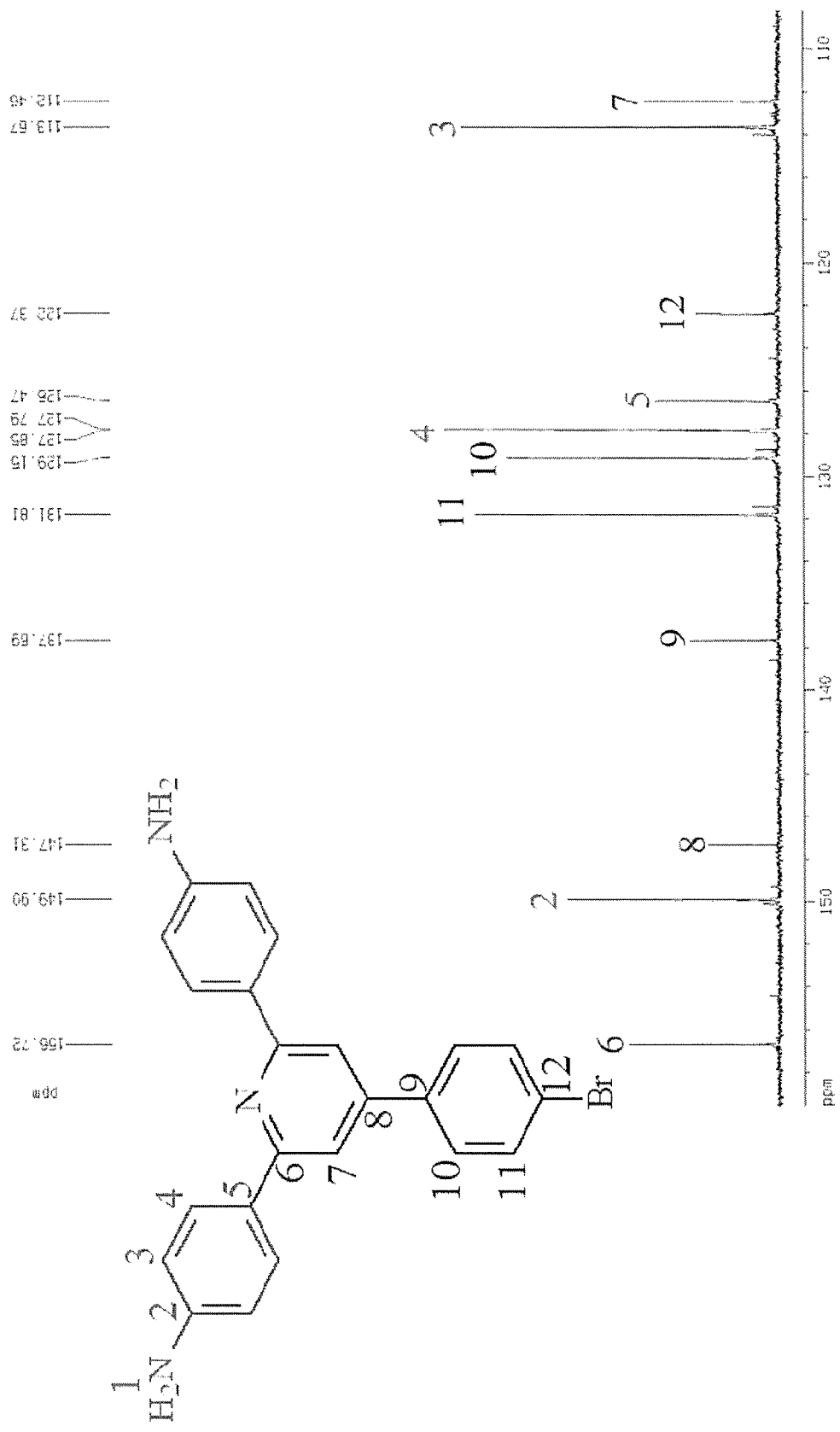
FIG. 2 is a $^{13}$C-NMR spectrum of diamine compound 2.

$^{13}$C-NMR DMSO-d$_6$: δ(ppm)=156.7, 149.9, 147.3, 137.7, 131.8, 129.2, 127.8, 126.5, 122.4, 113.7, 112.5, as shown in FIG. 2.

Elemental analysis: theoretical values (%): C=66.36, H=4.38, N=10.09. Analysis Values (%): C=66.34, H=4.40, N=10.20.

Step (3):
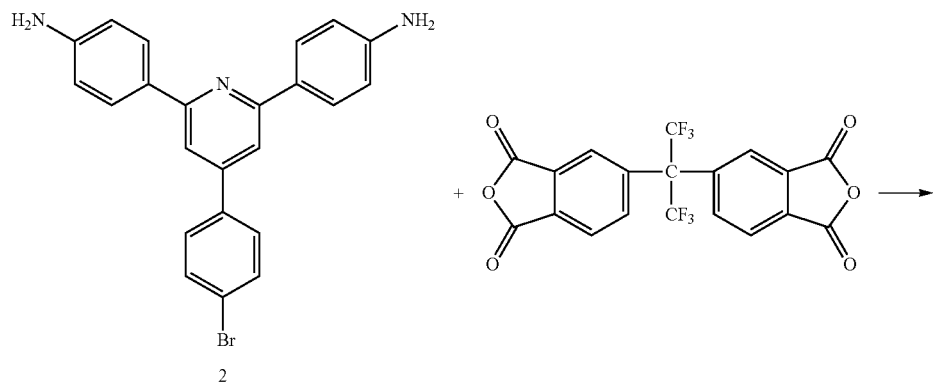
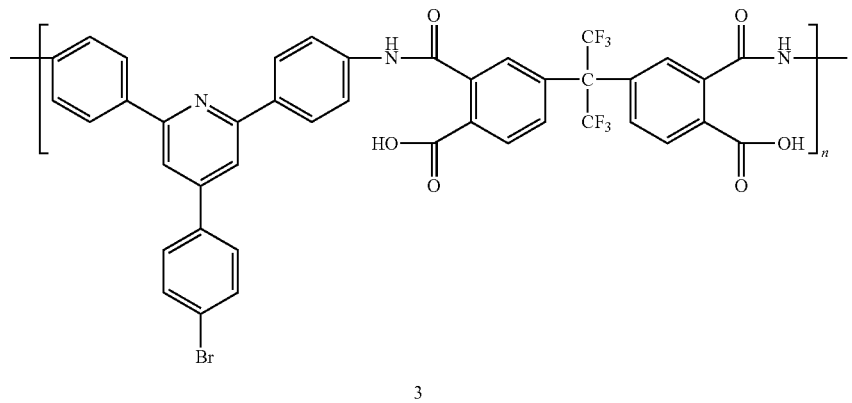
1.0 mmol of diamine compound 2 is dissolved in 5 ml of dehydrated N-methyl-2-pyrrolidone (NMP), and then 1.0 mmol of 4,4'-(hexafluoroisopropylidene)diphthalic anhydride (6FDA) is added to the solution in batches. The solution is stirred to react for 24 hours in room temperature to obtain intermediate product 3.
Step (4):
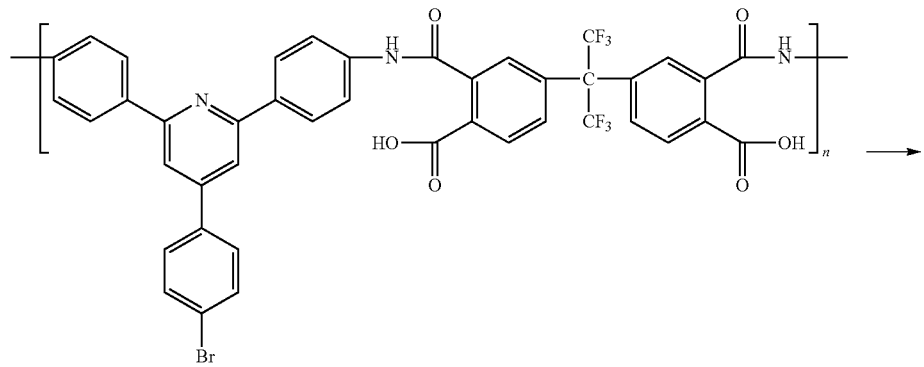

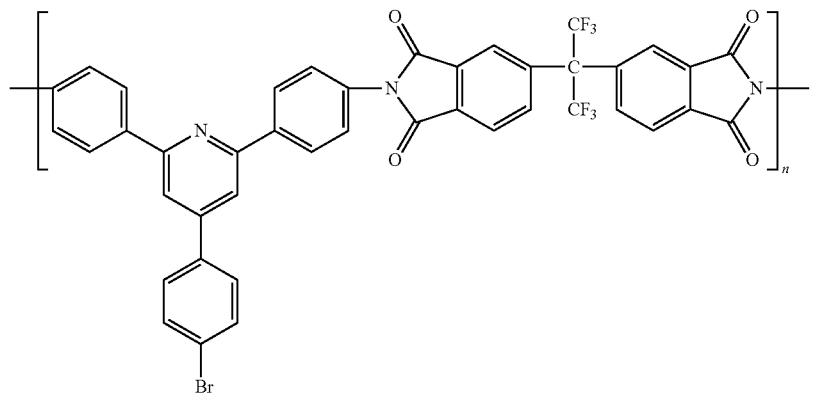

4

0.5 ml of pyridine and 1.0 ml of acetic anhydride are added to the solution of step (3) to react for 1 hour at room temperature. Then, the solution is heated to 100° C. and reacted in an environment at 100° C. for 4 hours for a cyclodehydration reaction in order to obtain polyimide compound 4. The yield is 97%. The following qualitative tests are performed on polyimide compound 4.

Infrared spectroscopy: the characteristic absorption peaks of the C=O are at 1785 and 1725 cm$^{-1}$, and the characteristic absorption peak of the C—N is at 1370 cm$^{-1}$.

Figure 3:
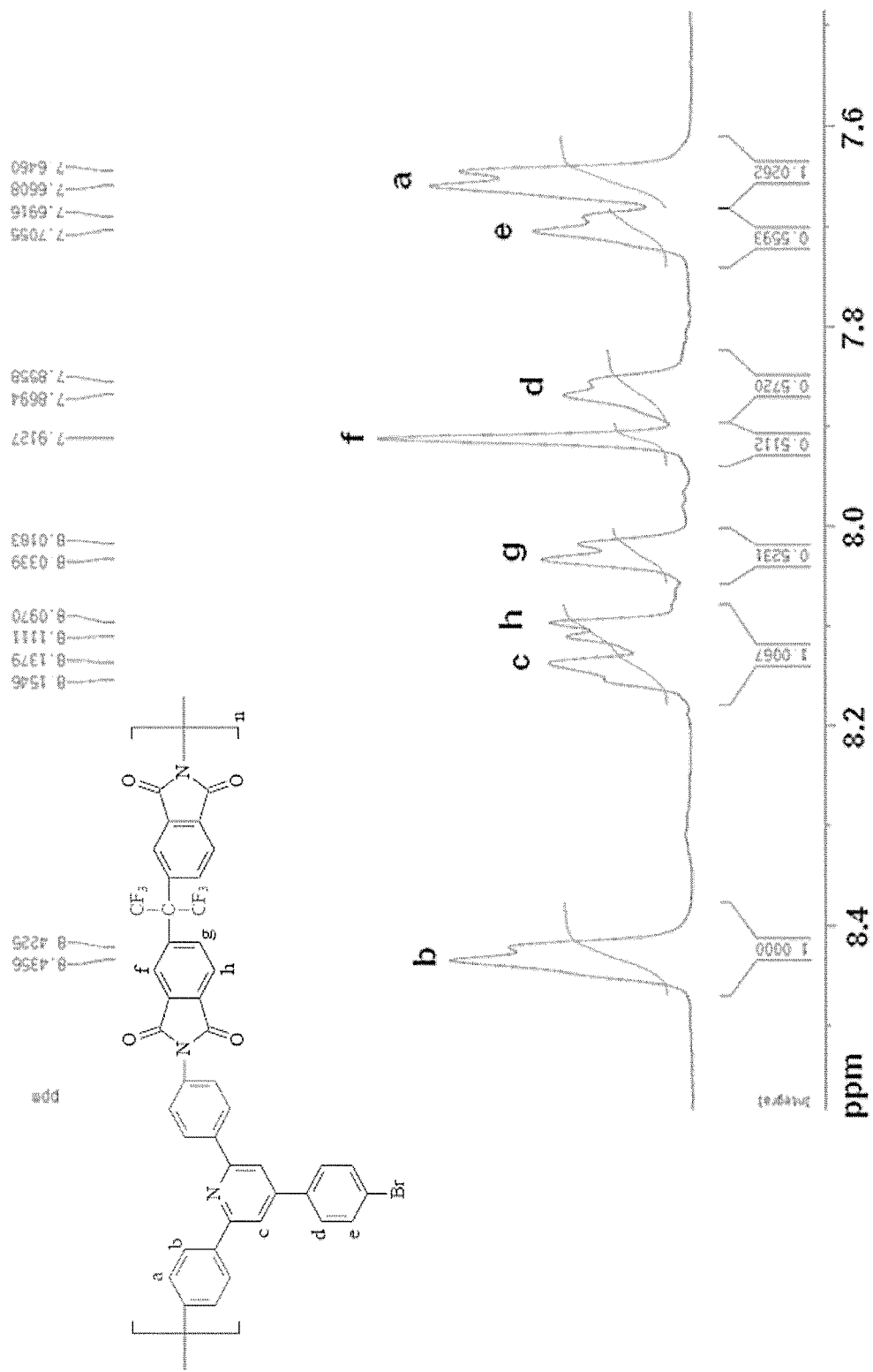
FIG. 3 is a $^1$H-NMR spectrum of polyimide compound 4.

$^1$H-NMR DMSO-d$_6$: δ(ppm)=8.43-8.42 (4H), 8.15-8.14 (2H), 8.11-8.09 (2H), 8.03-8.02 (2H), 7.91 (2H), 7.86-7.85 (2H), 7.70-7.69 (2H), 7.66-7.64 (4H), as shown in FIG. 3.

Figure 4:
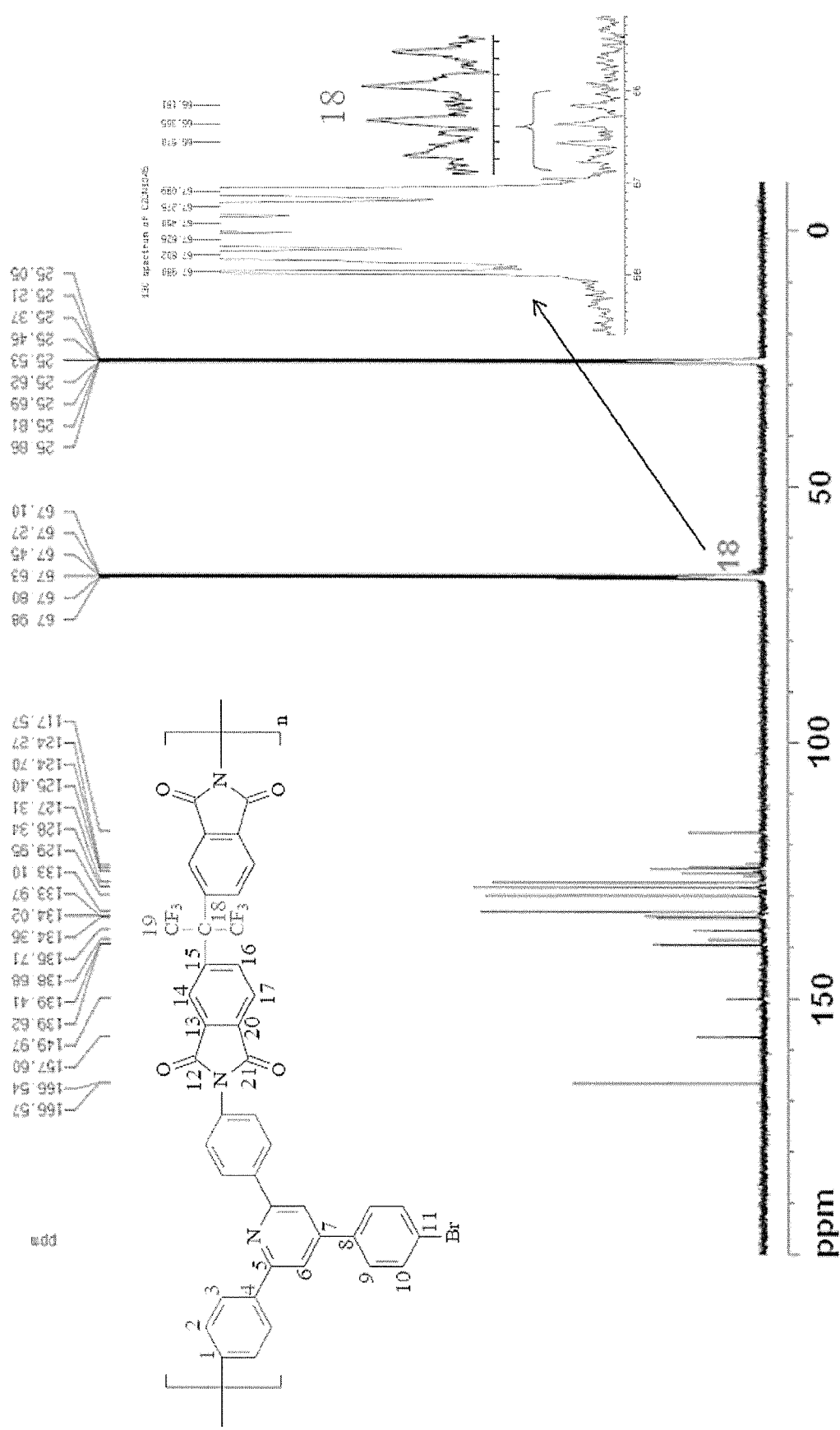
FIG. 4 is a $^{13}$C-NMR spectrum of polyimide compound 4.
Figure 5:
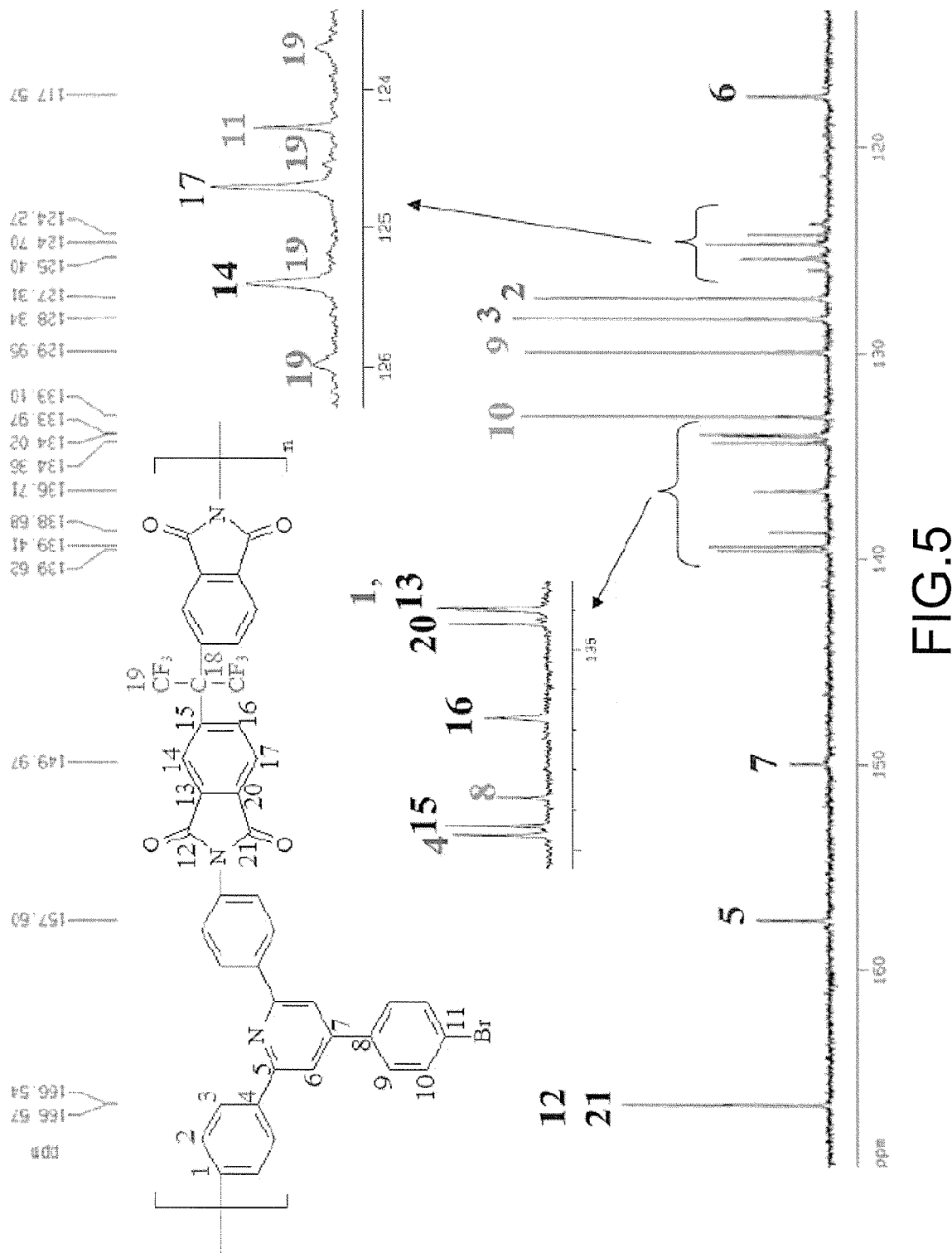
FIG. 5 is a $^{13}$C-NMR spectrum of polyimide compound 4.

$^{13}$C-NMR DMSO-d$_6$: δ(ppm)=166.57, 166.54, 157.60, 149.97, 139.62, 139.41, 138.68, 136.71, 134.35, 134.02, 133.97, 133.10, 129.95, 128.34, 127.31, 125.40, 124.70, 124.27, 117.57, 67.10, as shown in FIG. 4 and FIG. 5.

Elemental analysis: theoretical values (%): C=61.18, H=2.44, N=5.10. Analysis Values (%): C=60.30, H=2.74, N=4.92.

Step (5):

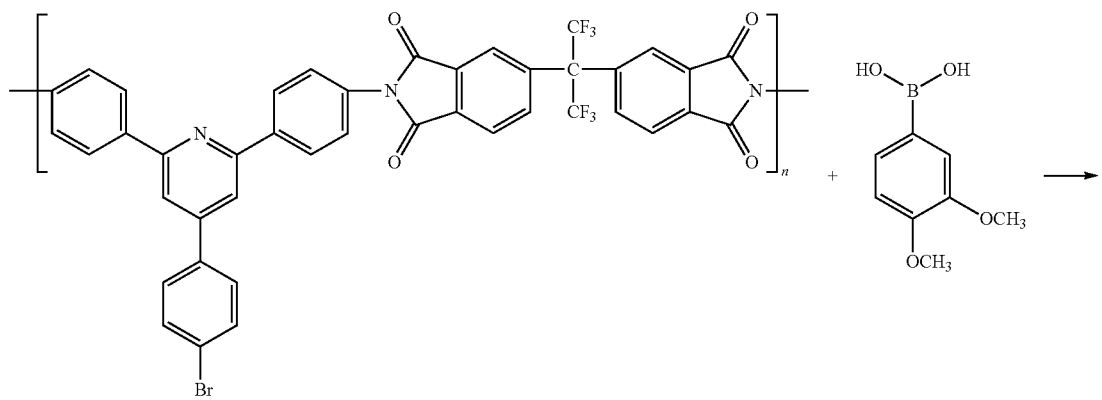

4

-continued

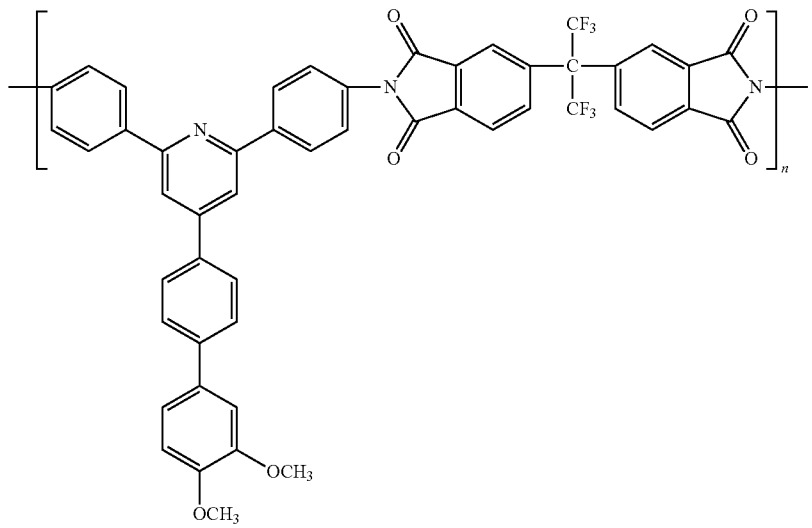

5

Figure 6:
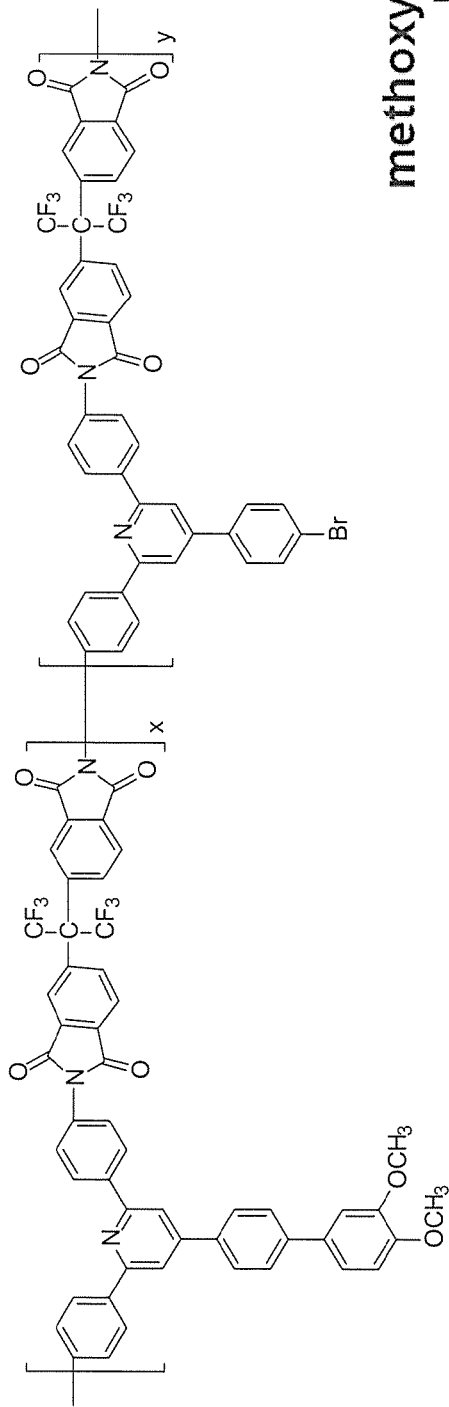
FIG. 6 is a $^1$H-NMR spectrum of modified polyimide compound 5.
Figure 6:
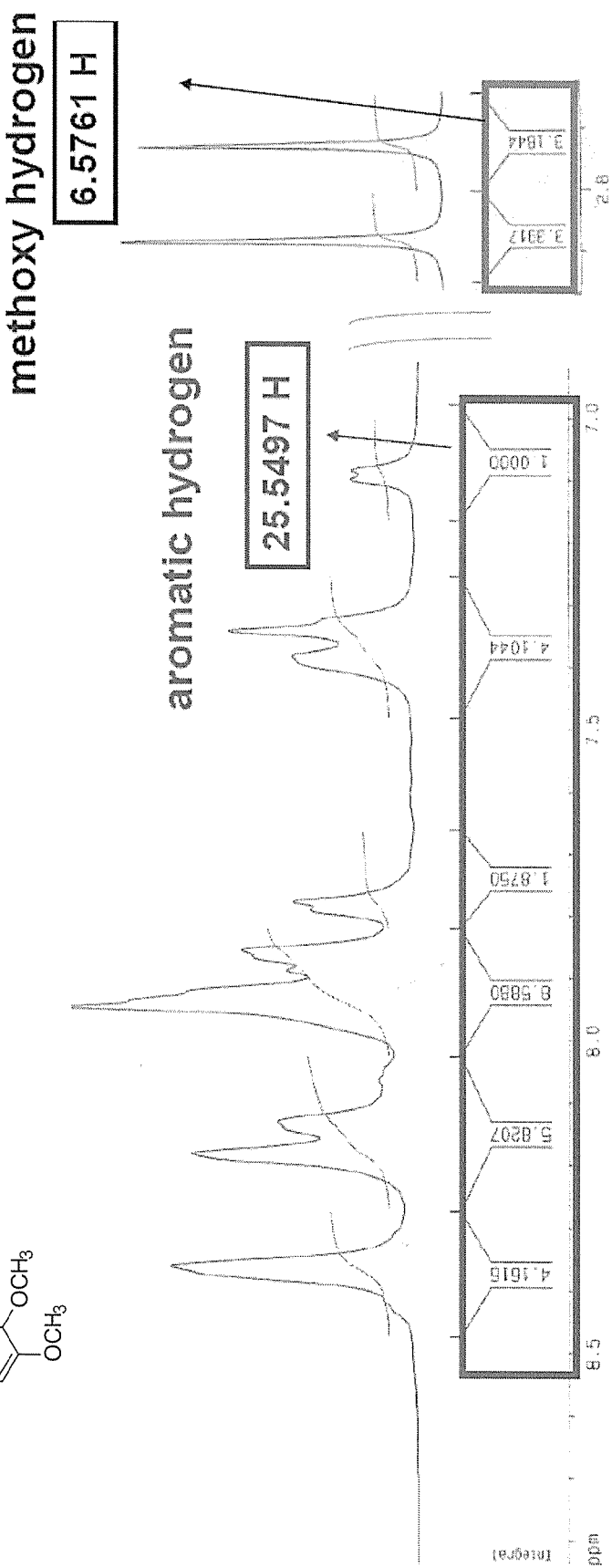

Then, 0.45 mmol of polyimide compound 4, 0.45 mmol of 3,4-dimethoxyphenylboronic acid, 10 ml of 2 M solution of sodium carbonate (Na$_2$CO$_{3(aq)}$), 10 ml of ethanol, and 10 ml of benzene are placed in a nitrogen reaction flask. Afterward, 1.34×10$^{-2}$ mmol of Pd(PPh$_3$)$_4$ is added, and the mixture solution is heated to 80° C. and refluxed for 6 hours. After the reaction is complete, the polymer solution is added to methanol to obtain polymer precipitate in a methanol solution. After the methanol solution is filtered, the product may be obtained and the product is rinsed with copious amounts of water. Then, the product is heated to 150° C. and dried under vacuum for 24 hours to obtain modified polyimide compound 5, wherein the $^1$H-NMR spectrum is as shown in FIG. 6. It is known from FIG. 6 that, modified polyimide compound 5 has an aromatic hydrogen signal and a methoxy hydrogen signal, thereby proving that polyimide compound 4 may indeed achieve the purpose of modification by experimental methods. For another perspective, please refer to the structure shown in Formula VIII and the integral value of the signal of FIG. 6, wherein x reaches 99%. In other words, the introduction ratio of an electron donating group containing a methoxy group into polyimide compound 4 may reach 99%.

CHARACTERISTICS EVALUATION

1. Characteristics Evaluation of Embodiment 1

Using polyimide compound 4 as embodiment 1, the following test structure is obtained after testing. In embodiment 1, the inherent viscosity is 0.603 dL/g, the molecular weight is 2.9×10$^4$, the tensile strength is 68 MPa, the elongation at break value is 9%, and the initial modulus is 1.87 GPa.

Figure 7:
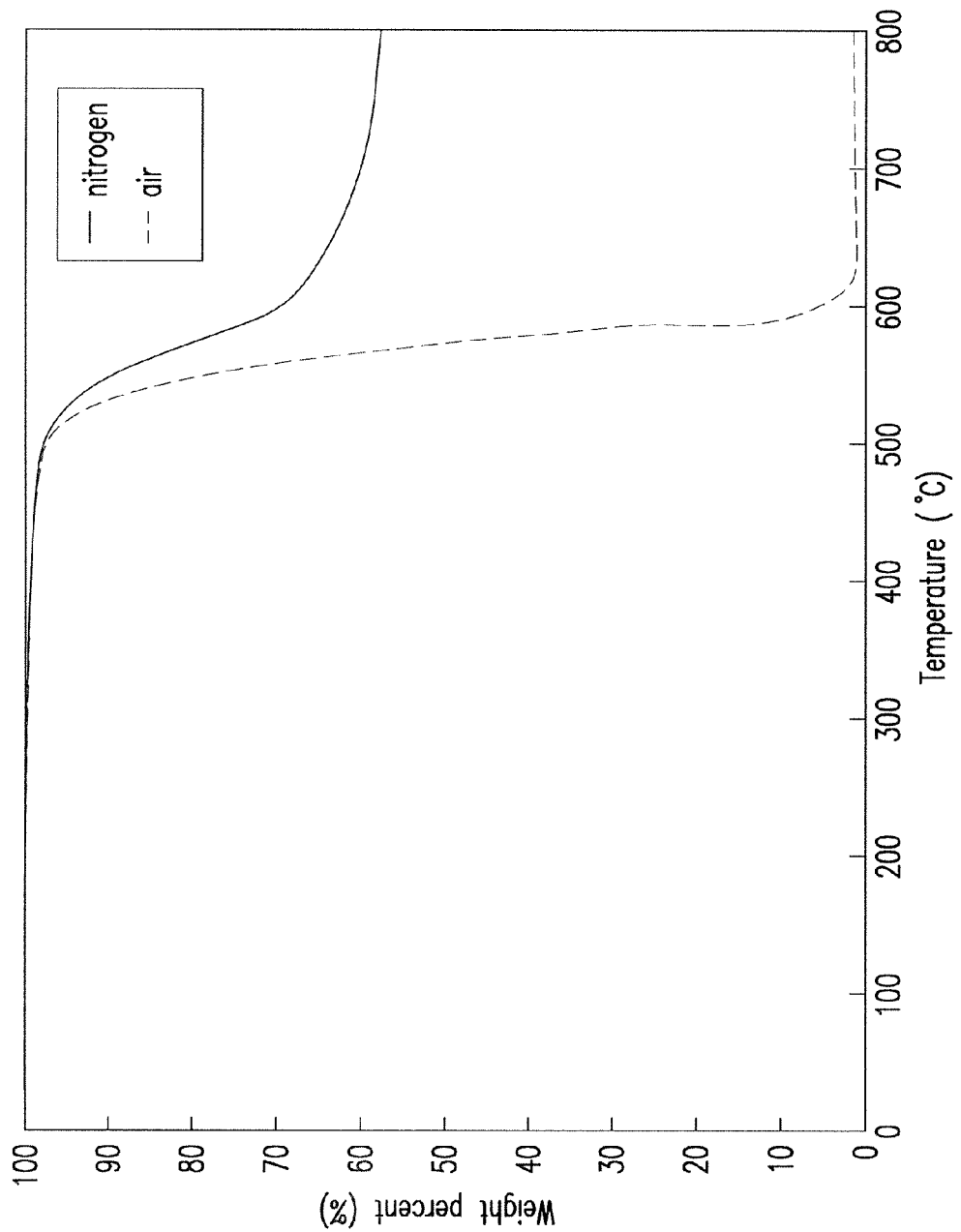
FIG. 7 is a TGA curve diagram obtained from the thermal gravimetric analysis of embodiment 1 in nitrogen and air.

FIG. 7 is a TGA curve diagram obtained from the thermal gravimetric analysis of embodiment 1 in nitrogen and air, wherein the decomposition temperature refers to the heating temperature when 10% by weight of the test sample is lost. Referring to FIG. 7, the decomposition temperature of embodiment 1 in nitrogen is 545° C., and the decomposition temperature of embodiment 1 in air is 530° C. It is acquired that the polyimide of embodiment 1 has good thermal stability.

2. Solubility Test of Embodiment 1, Embodiment 2, and Comparative Example 1

The structure of each of embodiment 1, embodiment 2, and comparative example 1 is listed in Table 1. The inherent viscosity of embodiment 2 is 0.55 dL/g, and the inherent viscosity of comparative example 1 is 0.72 dL/g. A solubility test is performed on embodiment 1, embodiment 2, and comparative example 1, and the results are as shown in Table 2.

TABLE 1

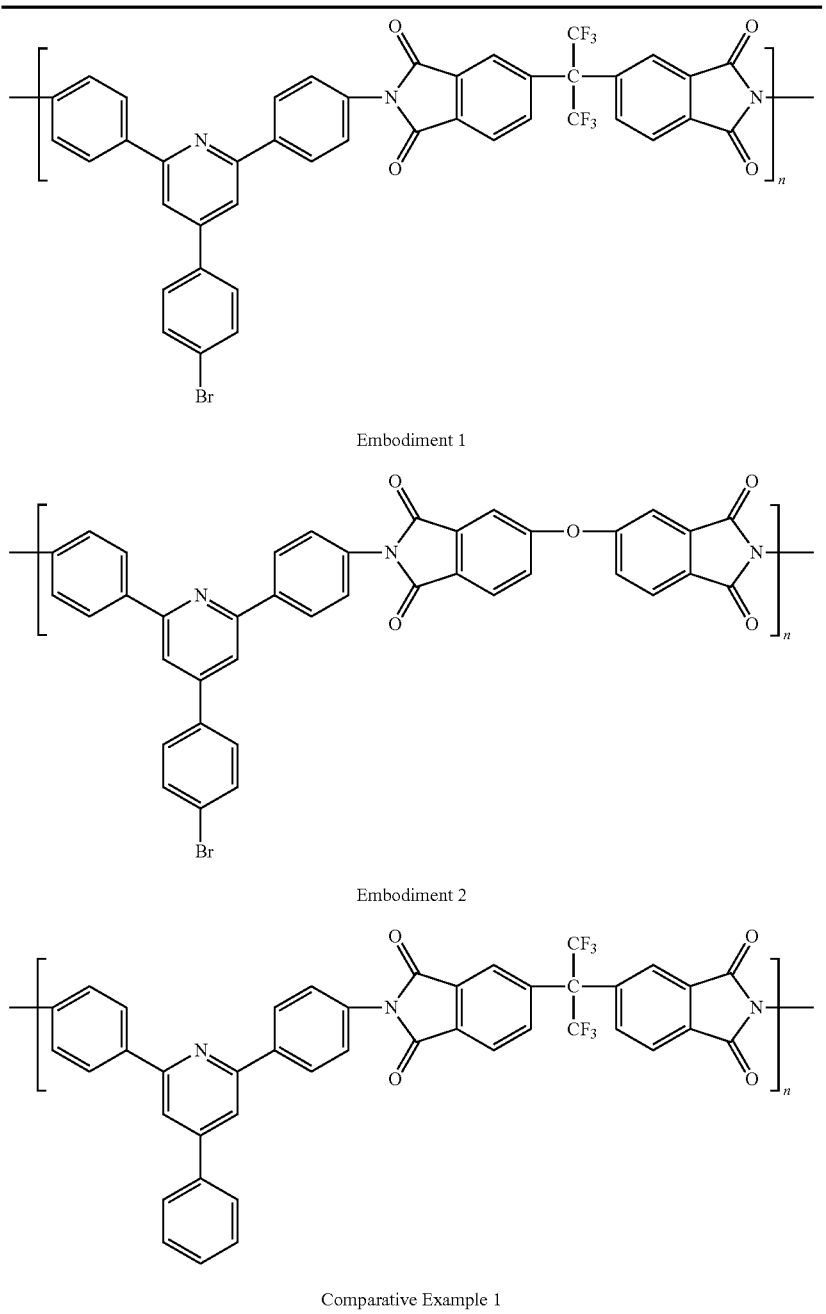

Embodiment 1

Embodiment 2

Comparative Example 1

TABLE 2

|  | NMP | DMAc | DMF | DMSO | THF | m-cresol |
|---|---|---|---|---|---|---|
| Embodiment 1 | ++ | ++ | ++ | ++ | ++ | ++ |
| Embodiment 2 | ++ | ++ | ++ | +− | +− | ++ |
| Comparative Example 1 | ++ | ++ | + | + | N/A | − |

In Table 2, ++ represents soluble at room temperature, + represents soluble after heating, +− represents partial soluble after heating, and − represents insoluble after heating. NMP is N-methyl-2-pyrrolidone. DMAc is N,N-dimethyl acetamide. DMF is dimethyl formamide. DMSO is dimethyl sulfoxide. THF is tetrahydrofuran. m-cresol is 3-methylphenol.

It is known from Table 2 that, generally, the polyimide of each of embodiment 1 and embodiment 2 has good solubility toward organic solvents.

3. Solubility Test of Embodiment 1 to Embodiment 20

Embodiment 1 to embodiment 13 are framed by the structure shown in Formula II, wherein X is Br and $A_1$ is the polyimide formed by Formula 1 to Formula 13. Table 3 shows the solubility test results of embodiment 1 to embodiment 13.

Embodiment 14 to embodiment 20 are framed by the structure shown in Formula V, wherein $A_1$ is the structure shown in Formula 1, and $A_2$ is the modified polyimide formed by Formula 19 to Formula 25. Table 4 shows the solubility test results of embodiment 14 to embodiment 20.

TABLE 3

|  | NMP | DMAc | DMF | DMSO | THF | m-cresol |
|---|---|---|---|---|---|---|
| Embodiment 1 | ++ | ++ | ++ | ++ | ++ | ++ |
| Embodiment 2 | ++ | ++ | ++ | +− | +− | ++ |
| Embodiment 3 | ++ | ++ | ++ | ++ | +− | ++ |
| Embodiment 4 | ++ | ++ | ++ | ++ | +− | +− |
| Embodiment 5 | ++ | ++ | ++ | +− | +− | +− |
| Embodiment 6 | ++ | ++ | ++ | ++ | +− | +− |
| Embodiment 7 | ++ | ++ | ++ | + | +− | +− |
| Embodiment 8 | ++ | ++ | ++ | ++ | +− | ++ |
| Embodiment 9 | ++ | ++ | ++ | +− | +− | ++ |
| Embodiment 10 | ++ | ++ | ++ | ++ | + | ++ |
| Embodiment 11 | ++ | ++ | ++ | ++ | +− | ++ |
| Embodiment 12 | ++ | ++ | ++ | +− | +− | +− |
| Embodiment 13 | ++ | ++ | ++ | ++ | −− | +− |

TABLE 4

|  | NMP | DMAc | DMF | DMSO | THF | m-cresol |
|---|---|---|---|---|---|---|
| Embodiment 14 | ++ | ++ | ++ | ++ | ++ | ++ |
| Embodiment 15 | ++ | ++ | ++ | ++ | +− | +− |
| Embodiment 16 | ++ | ++ | ++ | ++ | +− | ++ |
| Embodiment 17 | ++ | ++ | ++ | ++ | ++ | ++ |
| Embodiment 18 | ++ | ++ | ++ | ++ | ++ | ++ |
| Embodiment 19 | ++ | ++ | ++ | ++ | +− | +− |
| Embodiment 20 | ++ | ++ | ++ | ++ | +− | +− |

In Table 3 and Table 4, ++ represents soluble at room temperature, + represents soluble after heating, +− represents partial soluble after heating, and − represents insoluble after heating. It is known from Table 3 and Table 4 that, the unmodified polyimide has good solubility and the solubility of the modified polyimide may be further enhanced.

4. Viscosity Test of Embodiments 1 to 6 and Embodiments 12 to 20

A relative viscosity ($\eta_{rel}$) test and an inherent viscosity ($\eta_{inh}$) test are performed on the polyimide of each of embodiments 1 to 6 and embodiments 12 to 13 and the modified polyimide of each of embodiments 14 to 20, wherein each test sample is tested by dissolving in DMAc at a concentration of 0.5 g/dL and at 30° C. The test results are as shown in Table 5.

TABLE 5

|  | $\eta_{rel}$ (dL/g) | $\eta_{inh}$ (dL/g) |
|---|---|---|
| Embodiment 1 | 1.353 | 0.603 |
| Embodiment 2 | 1.201 | 0.550 |
| Embodiment 3 | 1.166 | 0.562 |
| Embodiment 4 | 1.214 | 0.568 |
| Embodiment 5 | 1.167 | 0.590 |
| Embodiment 6 | 1.385 | 0.651 |
| Embodiment 12 | 1.058 | 0.549 |
| Embodiment 13 | 1.027 | 0.542 |
| Embodiment 14 | 1.342 | 0.583 |
| Embodiment 15 | 1.338 | 0.593 |
| Embodiment 16 | 1.356 | 0.602 |
| Embodiment 17 | 1.344 | 0.597 |
| Embodiment 18 | 1.352 | 0.589 |
| Embodiment 19 | 1.320 | 0.579 |
| Embodiment 20 | 1.311 | 0.573 |

5. Glass Transition Temperature Test and Decomposition Temperature Test of Embodiments 1 to 7 and Embodiments 14 to 20

A glass transition temperature ($T_g$) test and a decomposition temperature ($T_d$) test are performed on the polyimide of each of embodiments 1 to 7 and the modified polyimide of each of embodiments 14 to 20, wherein the decomposition temperature refers to the heating temperature when 10% by weight of the test sample is lost. The test results are as shown in Table 6.

TABLE 6

|  | $T_g$ (° C.) | $T_d$ (° C.) In nitrogen | $T_d$ (° C.) In air |
|---|---|---|---|
| Embodiment 1 | — | 545 | 530 |
| Embodiment 2 | — | 505 | 497 |
| Embodiment 3 | — | 518 | 505 |
| Embodiment 4 | — | 520 | 509 |
| Embodiment 5 | — | 507 | 498 |
| Embodiment 6 | — | 509 | 501 |
| Embodiment 7 | — | 505 | 494 |
| Embodiment 14 | 231 | 533 | 516 |
| Embodiment 15 | 247 | 541 | 519 |
| Embodiment 16 | 205 | 530 | 514 |
| Embodiment 17 | 220 | 535 | 517 |
| Embodiment 18 | 221 | 532 | 517 |
| Embodiment 19 | 244 | 543 | 520 |
| Embodiment 20 | 253 | 545 | 523 |

"—" of the table: represents that glass transition temperature is not determined within 340° C.

6. Mechanical Property Test of Embodiments 1 to 13 and Embodiments 14 to 20

A mechanical property test is performed on the polyimide of each of embodiments 1 to 13 and the modified polyimide of each of embodiments 14 to 20, such as the tests of tensile strength, elongation at break value, and tensile modulus. The test method is: a thin film is formed by dissolving the polyimide of each of embodiments 1 to 13 and the modified polyimide of each of embodiments 14 to 20 in DMAc. A mechanical property test is then performed on each thin film. The test results are as shown in Table 7.

TABLE 7

|  | Tensile strength (MPa) | Elongation at break value (%) | Tensile modulus (GPa) |
|---|---|---|---|
| Embodiment 1 | 68 | 9 | 1.87 |
| Embodiment 2 | 69 | 8 | 1.77 |
| Embodiment 3 | 68 | 8 | 1.75 |
| Embodiment 4 | 68 | 9 | 1.82 |
| Embodiment 5 | 65 | 10 | 1.77 |
| Embodiment 6 | 72 | 13.5 | 2.23 |
| Embodiment 7 | 69 | 10 | 2.01 |
| Embodiment 8 | 67 | 8 | 1.92 |
| Embodiment 9 | 66 | 7 | 1.85 |
| Embodiment 10 | 66 | 7 | 1.83 |
| Embodiment 11 | 65 | 7 | 1.79 |
| Embodiment 12 | 65 | 8 | 1.75 |
| Embodiment 13 | 65 | 7 | 1.72 |
| Embodiment 14 | 68 | 9 | 1.87 |
| Embodiment 15 | 68 | 8 | 1.85 |
| Embodiment 16 | 67 | 8 | 1.80 |
| Embodiment 17 | 66 | 10 | 1.77 |
| Embodiment 18 | 66 | 11 | 1.75 |
| Embodiment 19 | 66 | 7 | 1.73 |
| Embodiment 20 | 66 | 7 | 1.70 |

Based on the above, a polyimide having a reactive group may be synthesized from the diamine monomer of the invention, and a modified polyimide may be obtained by introducing a functional group via the reaction of the polyimide having a reactive group. By introducing different functional groups, a modified polyimide having the desired properties may be obtained. Accordingly, the modified polyimide of the invention may have good solubility, thermal stability, superior processability, and mechanical property.

Although the invention has been described with reference to the above embodiments, it will be apparent to one of the ordinary skill in the art that modifications and variations to the described embodiments may be made without departing from the spirit and scope of the invention. Accordingly, the scope of the invention will be defined by the attached claims not by the above detailed descriptions.

What is claimed is:

1. A dinitro monomer, comprising a structure shown in Formula I:

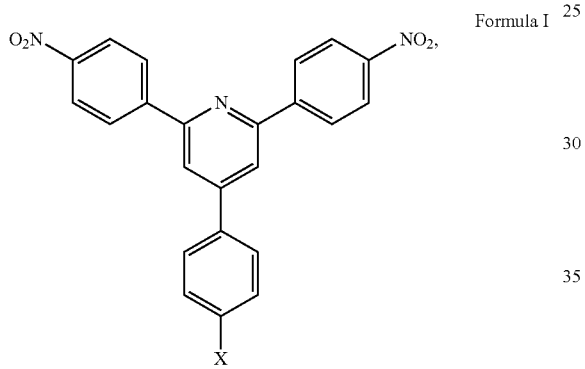

Formula I wherein X is halogen.

2. The dinitro monomer of claim 1, wherein X is F, Cl, Br, or I.

3. A diamine monomer, comprising a structure shown in Formula II:

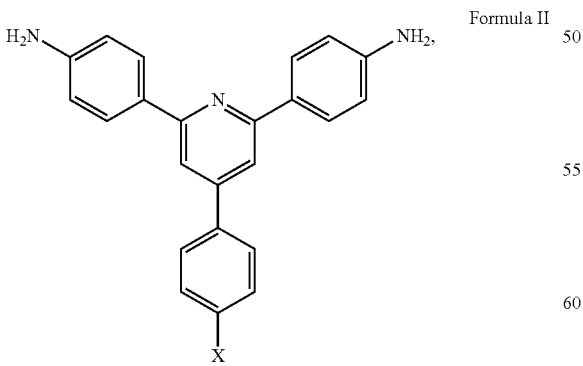

Formula II wherein X is halogen.

4. The diamine monomer of claim 3, wherein X is F, Cl, Br, or I.

5. A polyimide, comprising a structure shown in Formula III:

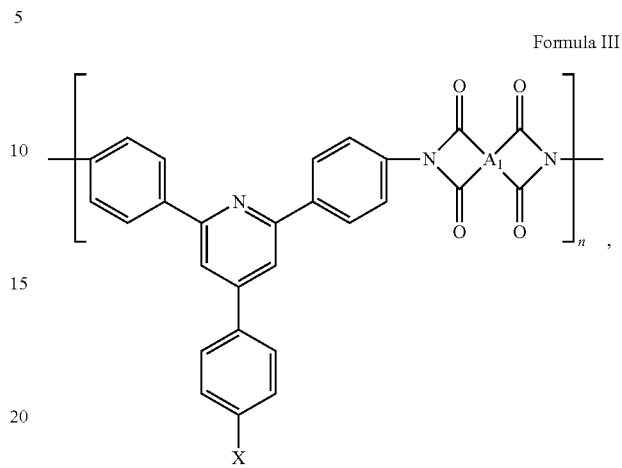

Formula III wherein X is halogen, $A_1$ is selected from one of Formula 1 to Formula 18, and n is 2 to 500,

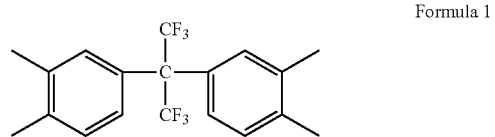

Formula 1

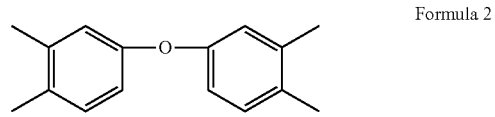

Formula 2

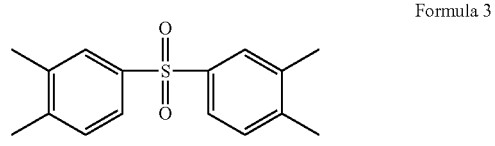

Formula 3

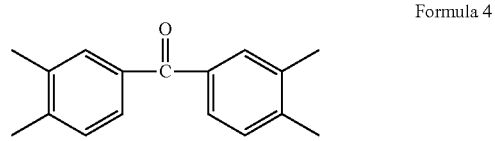

Formula 4

Formula 5

Formula 6
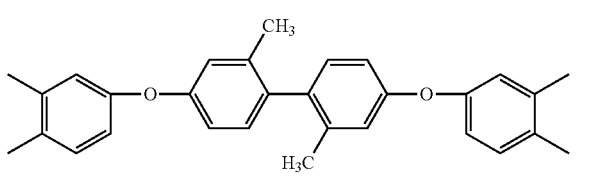
Formula 7
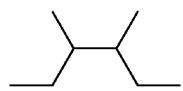
Formula 8
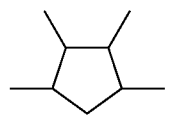
Formula 9
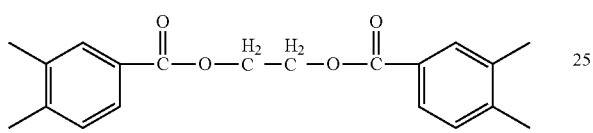
Formula 10
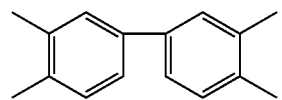
Formula 11
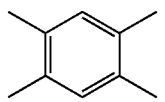
Formula 12
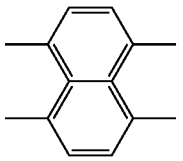
Formula 13
Formula 14
Formula 15
Formula 16
Formula 17
Formula 18
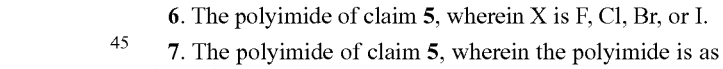
6. The polyimide of claim 5, wherein X is F, Cl, Br, or I.
7. The polyimide of claim 5, wherein the polyimide is as shown in Formula IV:
Formula IV
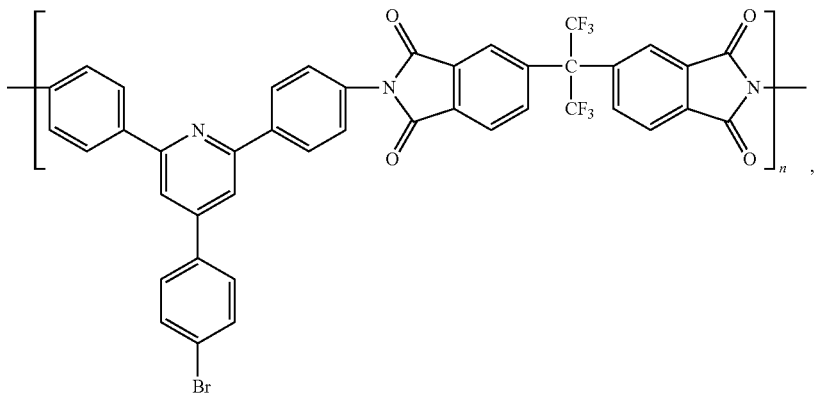
n is 2 to 500.

8. The polyimide of claim 5, wherein the polyimide is as shown in Formula V:

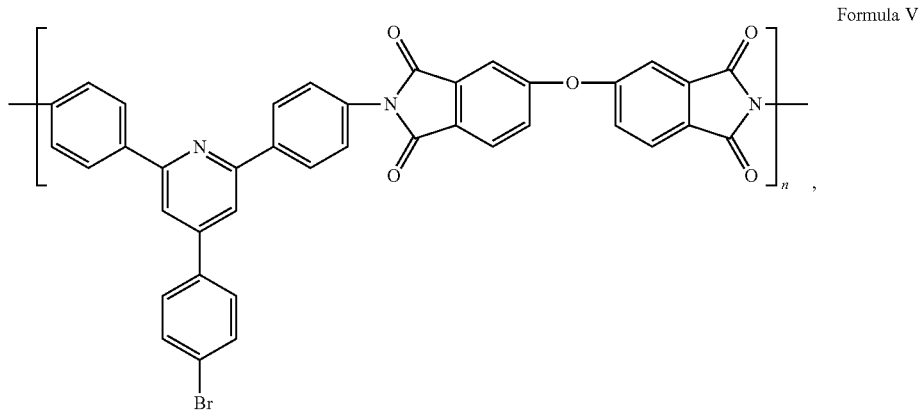

Formula V n is 2 to 500.

9. A modified polyimide, comprising a structure shown in Formula VI:

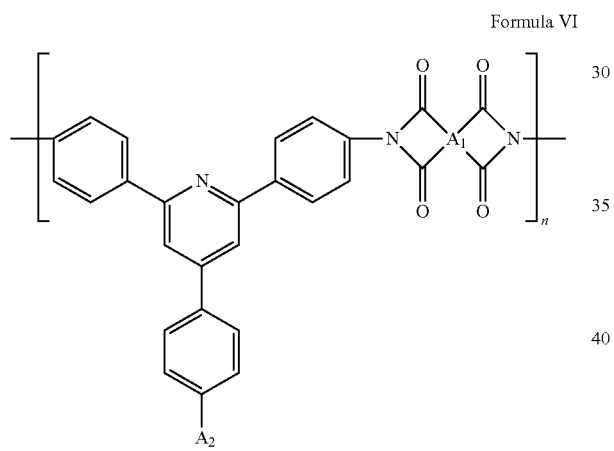

Formula VI wherein $A_1$ is selected from one of Formula 1 to Formula 18, $A_2$ is selected from one of Formula 19 to Formula 25, and n is 2 to 500,

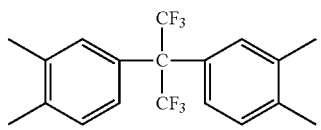

Formula 1

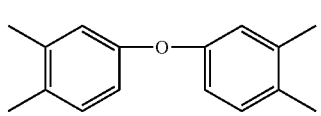

Formula 2

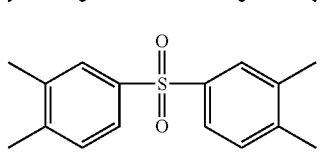

Formula 3

-continued

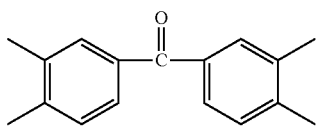

Formula 4

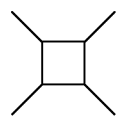

Formula 5

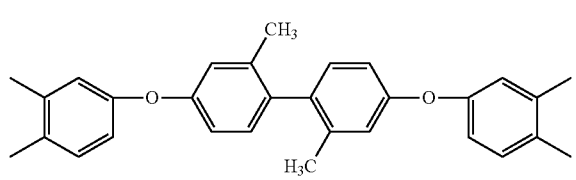

Formula 6

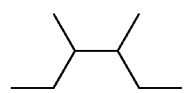

Formula 7

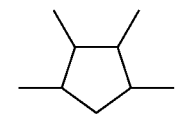

Formula 8

Formula 9

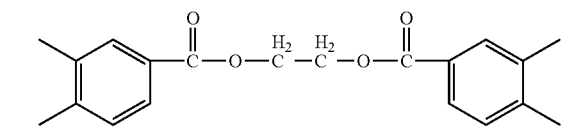

Formula 10

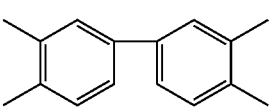

Formula 11

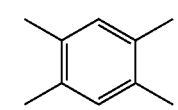

Formula 12
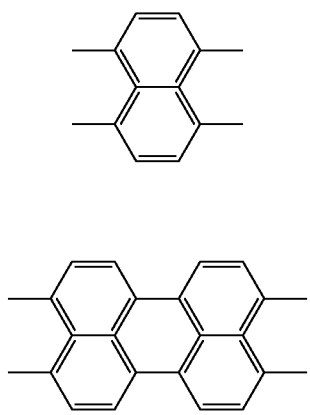
Formula 13
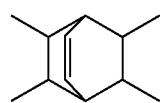
Formula 14
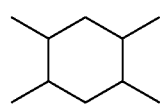
Formula 15
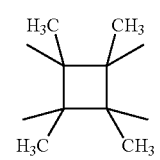
Formula 16
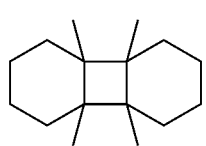
Formula 17
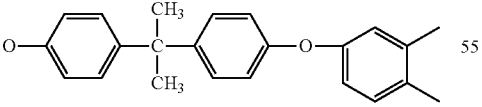
Formula 18
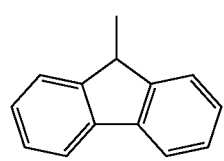
Formula 19
Formula 20
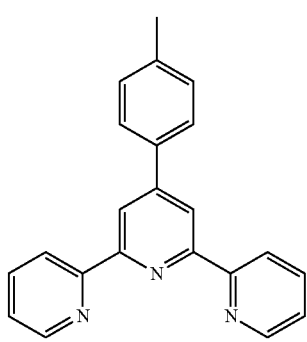
Formula 21
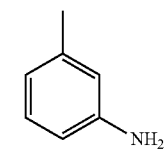
Formula 22
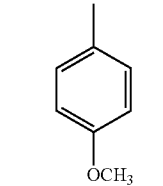
Formula 23
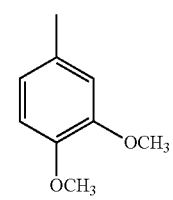
Formula 24
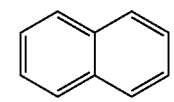
Formula 25
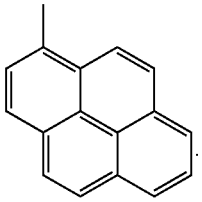
10. The modified polyimide of claim 9, wherein the modified polyimide is as shown in Formula VII:

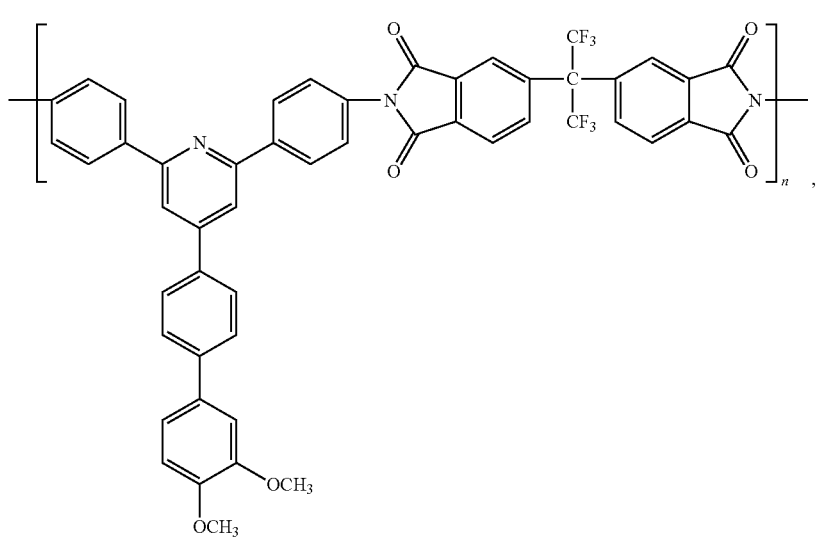
Formula VII
n is 2 to 500.
11. The modified polyimide of claim 9, wherein the modified polyimide is as shown in Formula VIII:
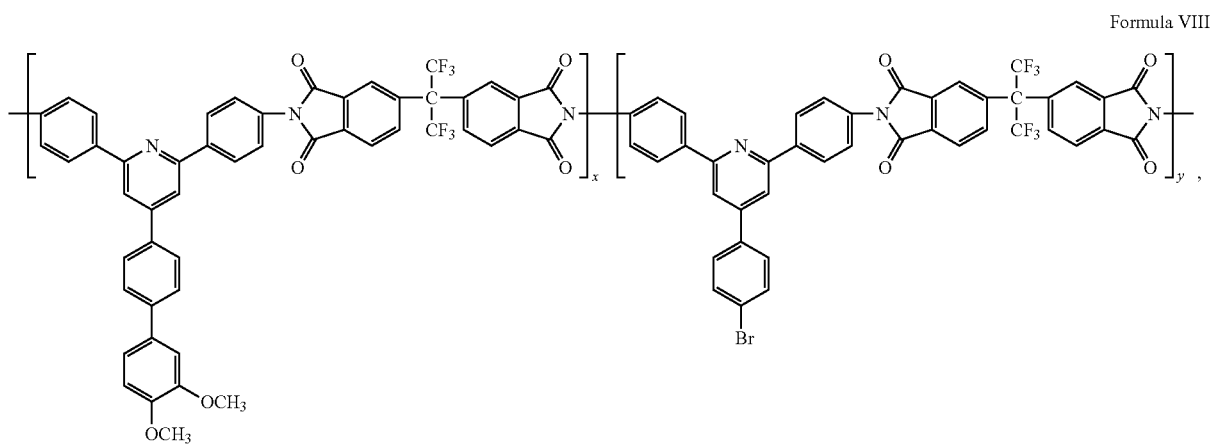
Formula VIII
X is 0% to 100%, y is 0% to 100%, wherein x and y are not both 0%.
\* \* \* \* \*